(12) United States Patent
Murray et al.

(10) Patent No.: US 11,771,472 B2
(45) Date of Patent: Oct. 3, 2023

(54) SUBLAMINAR BAND CLAMP

(71) Applicant: GLOBUS MEDICAL, INC., Audubon, PA (US)

(72) Inventors: Patrick Murray, Collegeville, PA (US); David Leff, Philadelphia, PA (US); Shawn Cox, Reading, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 16/666,988

(22) Filed: Oct. 29, 2019

(65) Prior Publication Data

US 2021/0121204 A1  Apr. 29, 2021

(51) Int. Cl.
*A61B 17/70* (2006.01)

(52) U.S. Cl.
CPC ...... *A61B 17/7032* (2013.01); *A61B 17/7008* (2013.01); *A61B 17/7022* (2013.01); *A61B 17/7035* (2013.01); *A61B 17/7041* (2013.01); *A61B 17/7049* (2013.01); *A61B 17/7053* (2013.01); *A61B 17/7056* (2013.01); *A61B 17/7071* (2013.01)

(58) Field of Classification Search
CPC .......................... A61B 17/7053; A61B 17/82
See application file for complete search history.

(56) References Cited

U.S. PATENT DOCUMENTS

| | | | | |
|---|---|---|---|---|
| 6,652,526 B1 * | 11/2003 | Arafiles | ............ | A61B 17/7032 606/264 |
| 6,783,527 B2 * | 8/2004 | Drewry | ............ | A61B 17/7031 606/254 |
| 9,314,275 B2 * | 4/2016 | Clement | ............ | A61B 17/7053 |
| 9,675,386 B2 * | 6/2017 | Akbarnia | ............ | A61B 17/8869 |
| 9,770,265 B2 * | 9/2017 | Jackson | ............ | A61B 17/683 |
| 10,548,639 B2 * | 2/2020 | Blakemore | ............ | A61B 17/701 |
| 2011/0230969 A1 * | 9/2011 | Biedermann | ...... | A61B 17/7059 606/289 |
| 2013/0268011 A1 * | 10/2013 | Rezach | ............ | A61B 17/7053 606/86 A |
| 2014/0094850 A1 | 4/2014 | Clement et al. | | |
| 2014/0257397 A1 | 9/2014 | Akbarnia et al. | | |
| 2016/0157896 A1 | 6/2016 | Palmer et al. | | |
| 2017/0086888 A1 | 3/2017 | Simpson et al. | | |
| 2018/0153591 A1 * | 6/2018 | Schafer | ............ | A61B 17/8869 |
| 2018/0353217 A1 | 12/2018 | Rice et al. | | |
| 2019/0046244 A1 | 2/2019 | Nguyen et al. | | |

FOREIGN PATENT DOCUMENTS

| | | |
|---|---|---|
| EP | 2777569 A1 | 9/2014 |
| JP | 2018529422 A | 10/2018 |

* cited by examiner

*Primary Examiner* — Lynnsy M Summitt

(57) ABSTRACT

Systems, methods, and devices for securing a sublaminar band are provided. A sublaminar band clamp system may include a first locking mechanism, a second locking mechanism, and a body. The body may include a first portion comprising a first passage, wherein the first locking mechanism is disposed within the first passage. The body may further include a second portion comprising a second passage, wherein the second locking mechanism is disposed within the second passage. A third passage may extend across the body and may be in fluid communication with the second passage. An opening may be positioned between the first and second portions, and the opening may be in fluid communication with the first passage.

13 Claims, 31 Drawing Sheets

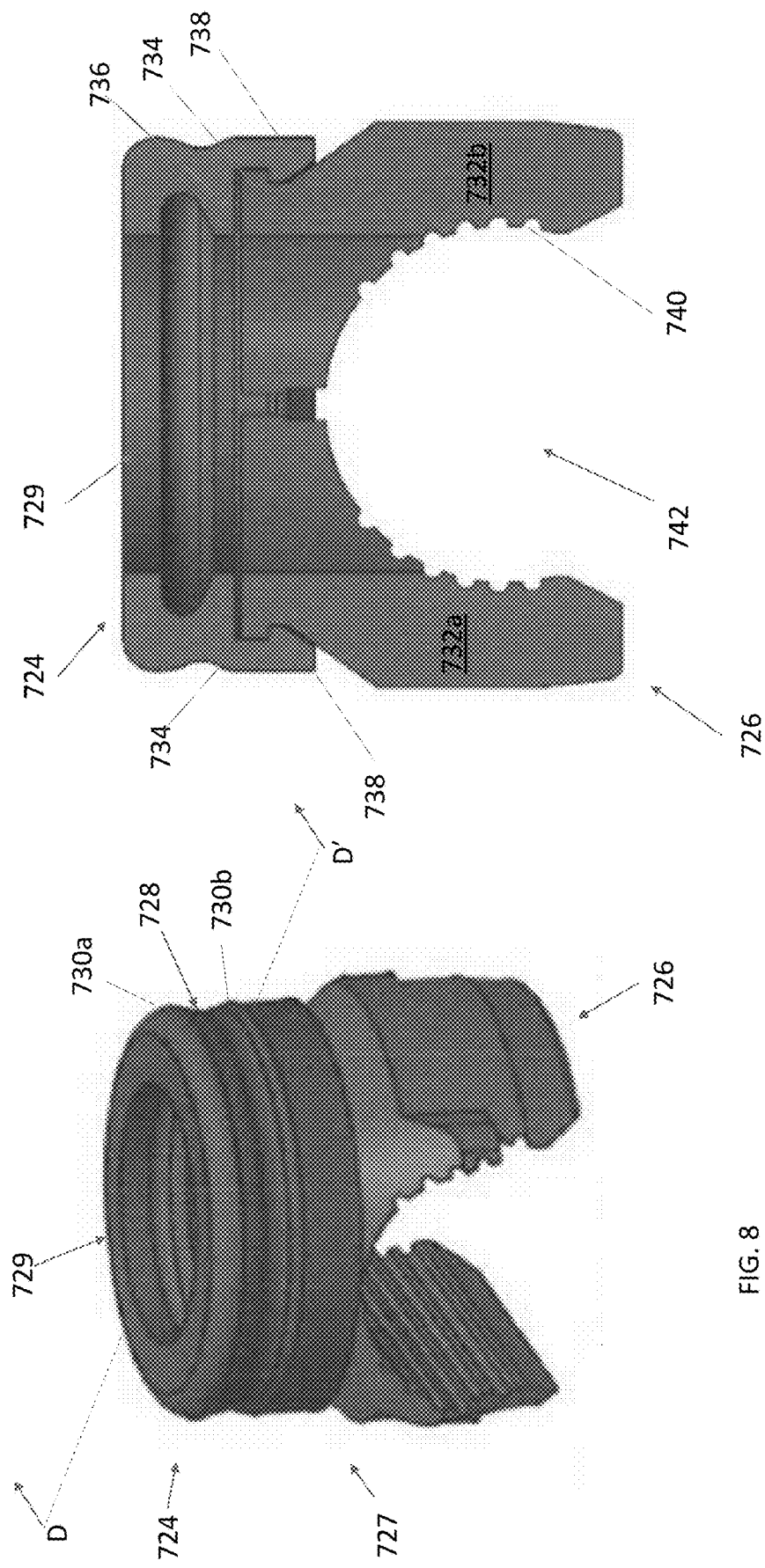

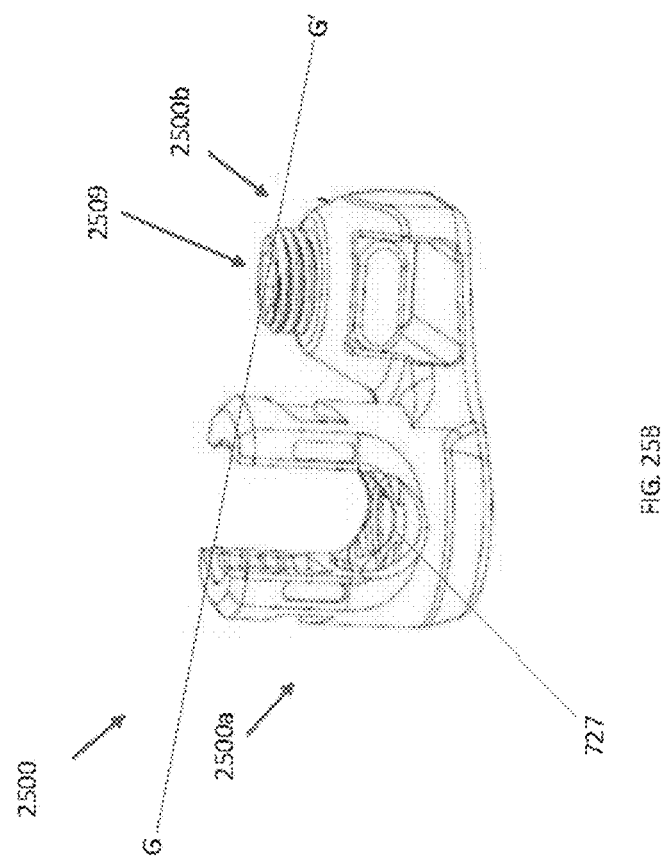
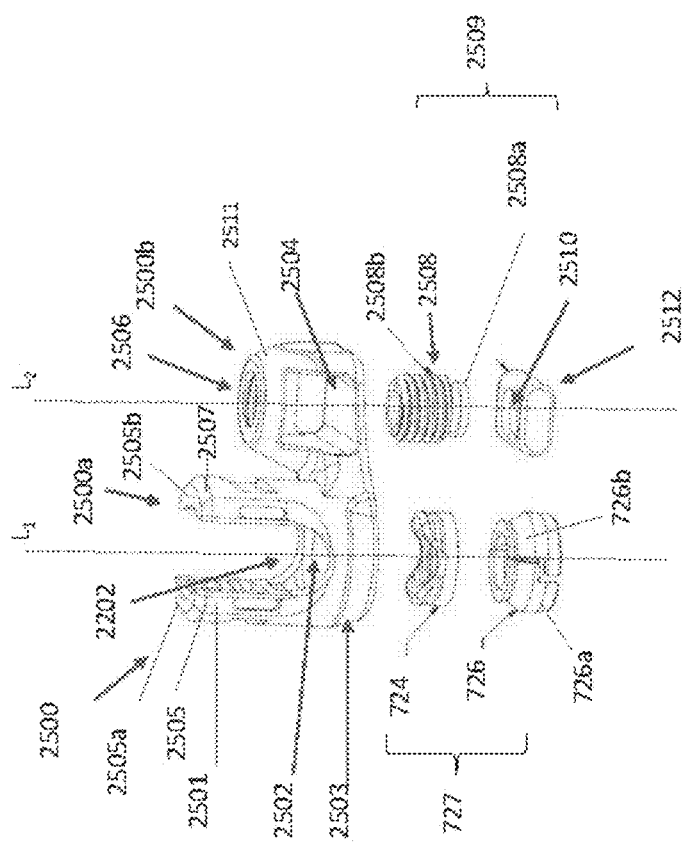
FIG. 25A
FIG. 25B

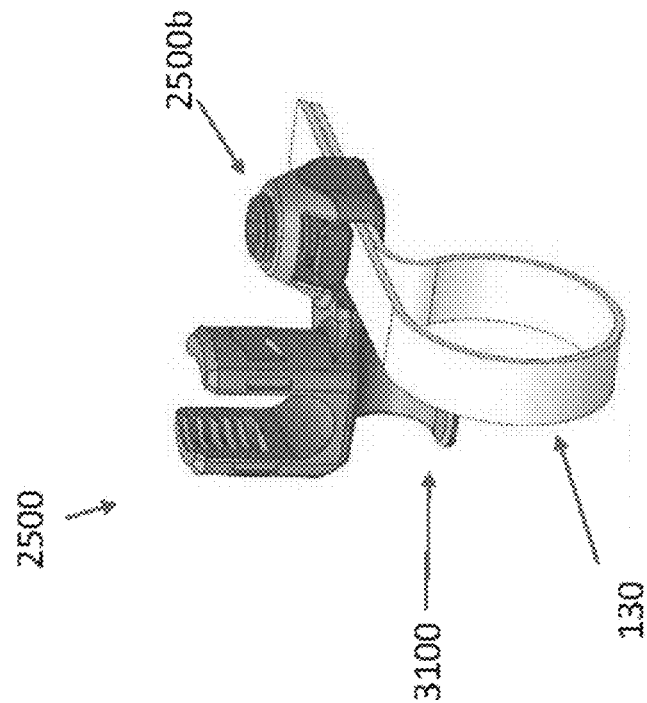
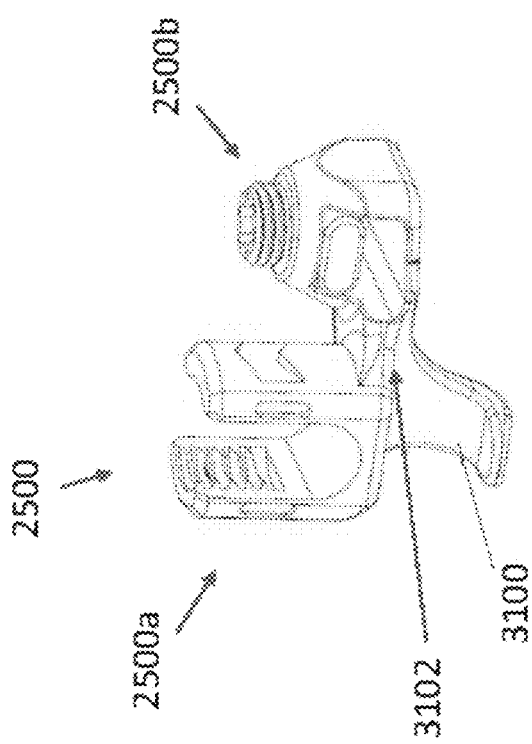
FIG. 31B
FIG. 31A

SUBLAMINAR BAND CLAMP

BACKGROUND

Many types of spinal irregularities cause pain, limit range of motion, or injure the nervous system within the spinal column. These irregularities can result from trauma, tumor, disc degeneration, or disease. Typically, these irregularities are treated by immobilizing a portion of the spine. This treatment typically involves affixing a plurality of components, such as, for example, screws, hooks, and/or clamps, to one or more vertebrae, and attaching the components to an elongated rod that stabilizes the vertebrae.

SUMMARY

In an exemplary embodiment, the present disclosure provides a sublaminar band clamp system that may include a first locking mechanism, a second locking mechanism, and a body. The body may include a first portion comprising a first passage, wherein the first locking mechanism is disposed within the first passage. The body may further include a second portion comprising a second passage, wherein the second locking mechanism is disposed within the second passage. A third passage may extend across the body and may be in fluid communication with the second passage. An opening may be positioned between the first and second portions, and the opening may be in fluid communication with the first passage.

In another exemplary embodiment, the present disclosure provides a sublaminar band clamp system that may include a tulip comprising a passage and a chamber fluidly coupled to the passage. A protrusion may extend inward from an inner surface of the chamber. A locking mechanism may be movably disposed within the chamber. The locking mechanism may include a saddle comprising a groove and a clamp. The saddle may be coupled to the clamp.

In another exemplary embodiment, the present disclosure provides a sublaminar band clamp system that may include a spinal rod comprising an elongated portion, and a clamp positioned at a first end of the spinal rod. The clamp may include a passage that extends in a direction from the first end to a second end of the spinal rod. The sublaminar band system may also include a locking mechanism extending toward the passage.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

These drawings illustrate certain aspects of some of the embodiments of the present disclosure and should not be used to limit or define the disclosure.

FIG. 8 illustrates a locking mechanism of the clamp system of FIG. 7, in accordance with embodiments of the present disclosure;

FIG. 9 is a cross-section of FIG. 8;

FIG. 25A illustrates separate components of a clamp system in accordance with embodiments of the present disclosure;

FIG. 25B illustrates the clamp system of FIG. 25A in an assembled configuration, in accordance with embodiments of the present disclosure;

FIG. 31A illustrates a clamp system including a hook, in accordance with embodiments of the present disclosure;

FIG. 31B illustrates the clamp system of FIG. 31A with a sublaminar band secured therein, in accordance with embodiments of the present disclosure;

DETAILED DESCRIPTION

Figure 1:
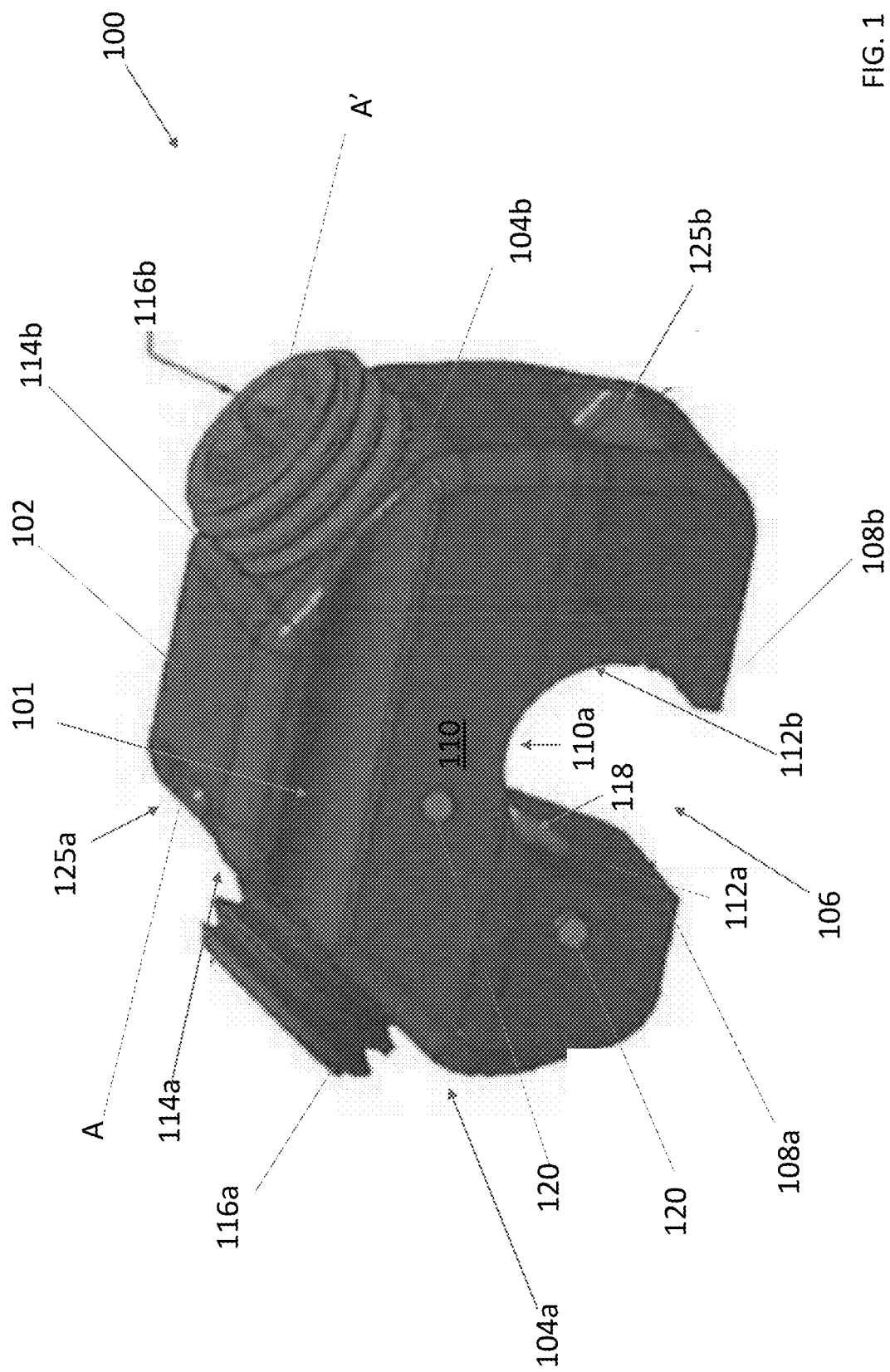
FIG. 1 illustrates a sublaminar band clamp ("clamp") in accordance with embodiments of the present disclosure.

For the purposes of promoting an understanding of the principles of the present disclosure, reference will now be made to the implementations illustrated in the drawings and specific language will be used to describe them. It will nevertheless be understood that no limitation of the scope of the disclosure may be intended. Any alterations and further modifications to the described devices, instruments, methods, and any further application of the principles of the present disclosure are fully contemplated as would normally occur to one skilled in the art to which the disclosure relates. In particular, it may be fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

Embodiments generally relate to spinal surgery. More particularly, embodiments relate to systems, methods, and devices for fixating spinal anatomy with a sublaminar band.

Sublaminar bands should be understood by one having skill in the art. The sublaminar bands may be utilized to provide posterior fixation of the spine as an alternative to pedicle screw instrumentation. They may be used in patients with poor bone quality or difficult anatomy where an interface between a bone and an implant is compromised. Patients with pediatric deformity often times have dysmorphic vertebrae, which restrict the use of pedicle screws. Additionally, the risk of screw pullout is increased in patients with osteoporosis due to weak connection between the bone and the implant. Also, the sublaminar bands may be used in cases where patients have fractured pedicles. In these clinical scenarios, the sublaminar bands offer an advantage of contacting the cortical bone of the lamina instead of relying on the cancellous bone within the pedicle and vertebral body. Alternatively, sublaminar bands may be wrapped around the lamina and transverse process to create a figure eight pattern.

FIG. 1 illustrates a sublaminar band clamp ("clamp") 100 in accordance with particular embodiments of the present disclosure. The clamp 100 may be a rigid member including a body 101. The body 101 may include a nose portion 102. The nose portion 102 may include a planar wall or surface. The body 101 may also include portions 104a and 104b that may extend from the nose portion 102, thereby forming an opening 106 between distal ends 108a and 108b of the portions 104a and 104b. The opening 106 may extend from between the distal ends 108a and 108b to (or at least partially through) a central portion 110 of the clamp 100, as shown. The opening 106 may be bound by inner surfaces 112a, 112b, and 110a of the portions 104a, 104b, and the central portion 110, respectively. In certain embodiments, the clamp 100 may generally be C-shaped or U-shaped and/or the opening 106 may generally be of or include a cylindrical shape or a portion thereof.

An outer portion 114a of the portion 104a may include a first clamping mechanism 116a (e.g., a set screw) which may extend through a passage 118 which extends through and from outer surface portion 114a to and through the inner surface 112a, as shown. That is, the passage 118 is in fluid communication with the opening 106. Pins 120 extend through the passage 118 to prevent the first clamping mechanism 116a from being removed from the passage 118. For example, the pins 120 may extend orthogonally, relative to a longitudinal axis of the passage 118, to prevent the first clamping mechanism 116a (e.g., the set screw) from being backed out or completely rotated out of the passage 118. The first clamping mechanism 116a may secure a spinal rod (e.g., spinal rod 128 shown on FIG. 3) within the opening 106.

Figure 2:
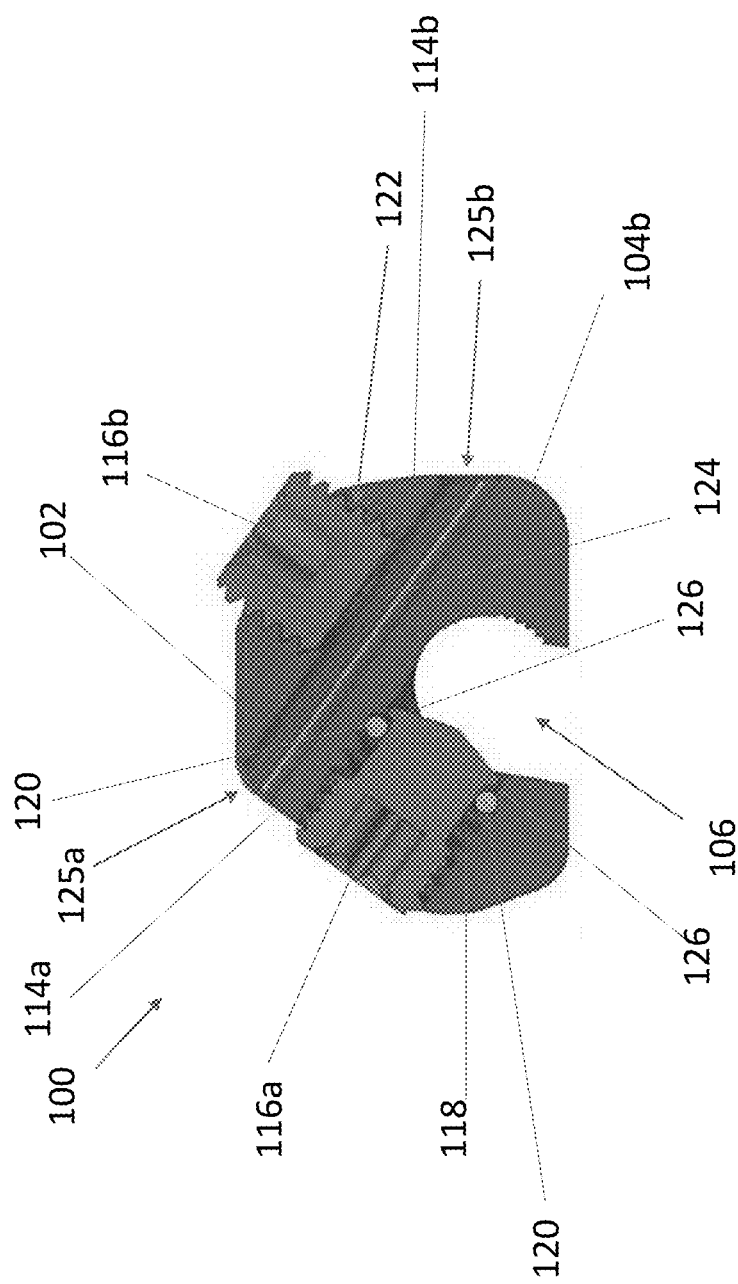
FIG. 2 is a cross-section of FIG. 1.

FIG. 2 is a cross-section, of the clamp 100 of FIG. 1, taken along the dashed line extending between A and A' (as shown on FIG. 1). As shown on FIG. 2, an outer portion 114b of the portion 104b may include a second clamping mechanism 116b (e.g., a set screw) which may extend through a passage 122. The passage 122 extends from the outer surface portion 114b to an internal conduit ("conduit") 124. The passage 122 may be in fluid communication with the conduit 124. In certain embodiments, the passage 122 may extend orthogonally from the conduit 124, as shown. The inner conduit 124 extends internally between the portion 104b and a portion of the nose portion 102 and may include an opening 125a at the nose portion 102 and may also include an opening 125b on outer portion 114b. The passage 124 extends between the openings 125a and 125b. The second clamping mechanism 116b may secure a portion of the sublaminar band (e.g., sublaminar band 130 as shown on FIG. 3) within the inner conduit 124. Both the clamping mechanisms 116a and 116b may be movable in a forward direction (e.g., toward a center of the clamp 100) and a reverse direction.

The passages 118 and 122 may be threaded. Also, as previously noted, the pins 120 may extend through the passage 118. As shown, a lip 126 at a distal end of the first clamping mechanism 116a is positioned adjacent to the pins 120. The lip 126 is positioned between the pins 120 and the opening 106, thereby preventing the first clamping mechanism 116a from being completely removed from the passage 118.

Figure 3:
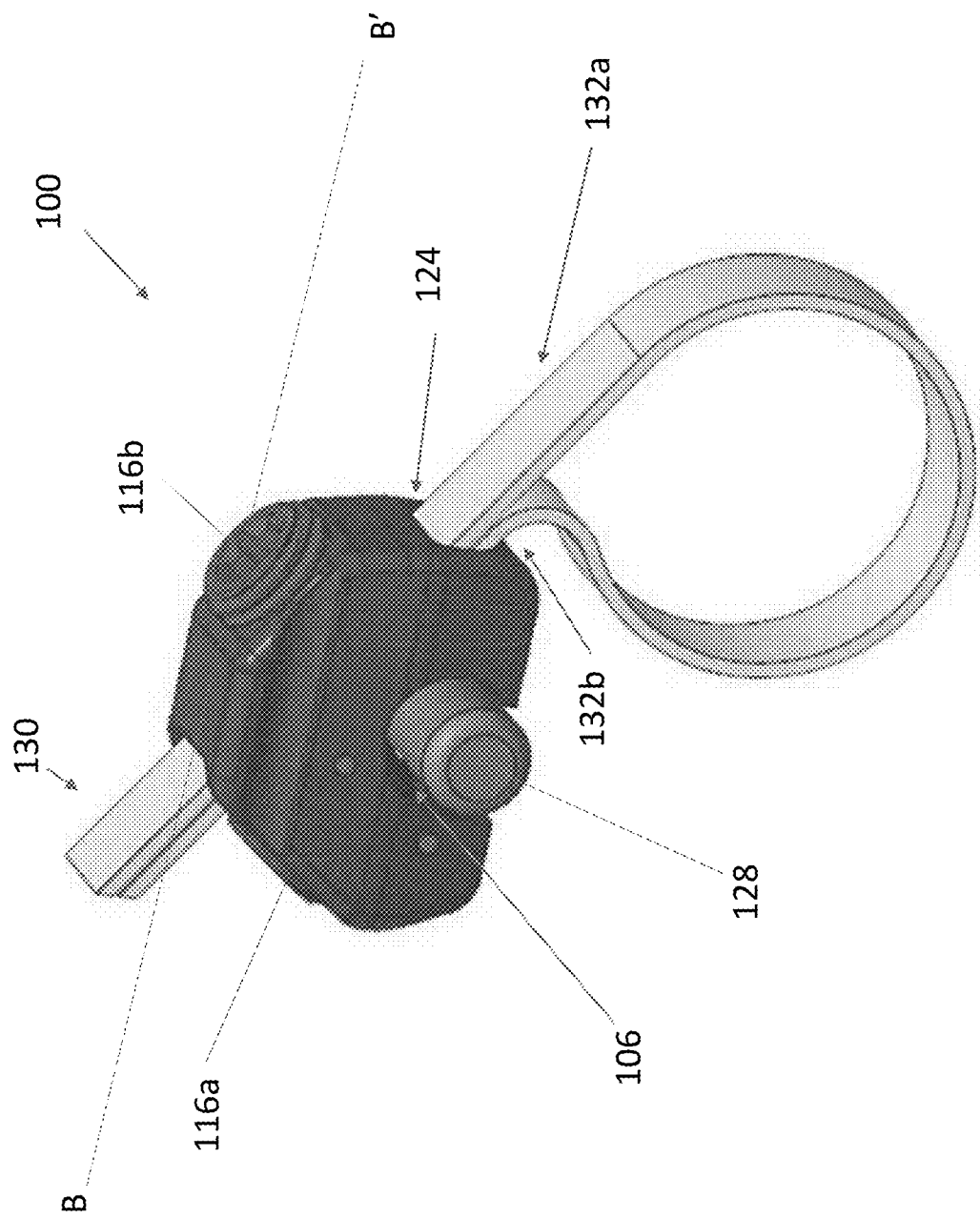
FIG. 3 illustrates the clamp of FIG. 1 with a spinal rod and a sublaminar band, in accordance with embodiments of the present disclosure.

FIG. 3 illustrates the clamp 100 with a spinal rod 128 and a sublaminar band 130 in accordance with particular embodiments of the present disclosure. As shown, the spinal rod 128 may extend through the opening 106 of the clamp 100. The first clamping mechanism 116a may be tightened or moved forward to press the spinal rod 128 against the inner surface 112b thereby securing the spinal rod 128 within the opening 106.

The sublaminar band 130 may extend through the passage 124. The sublaminar band 130 may be folded or curved and may include portions 132a and 132b which are stacked upon each other, as shown.

Figure 4:
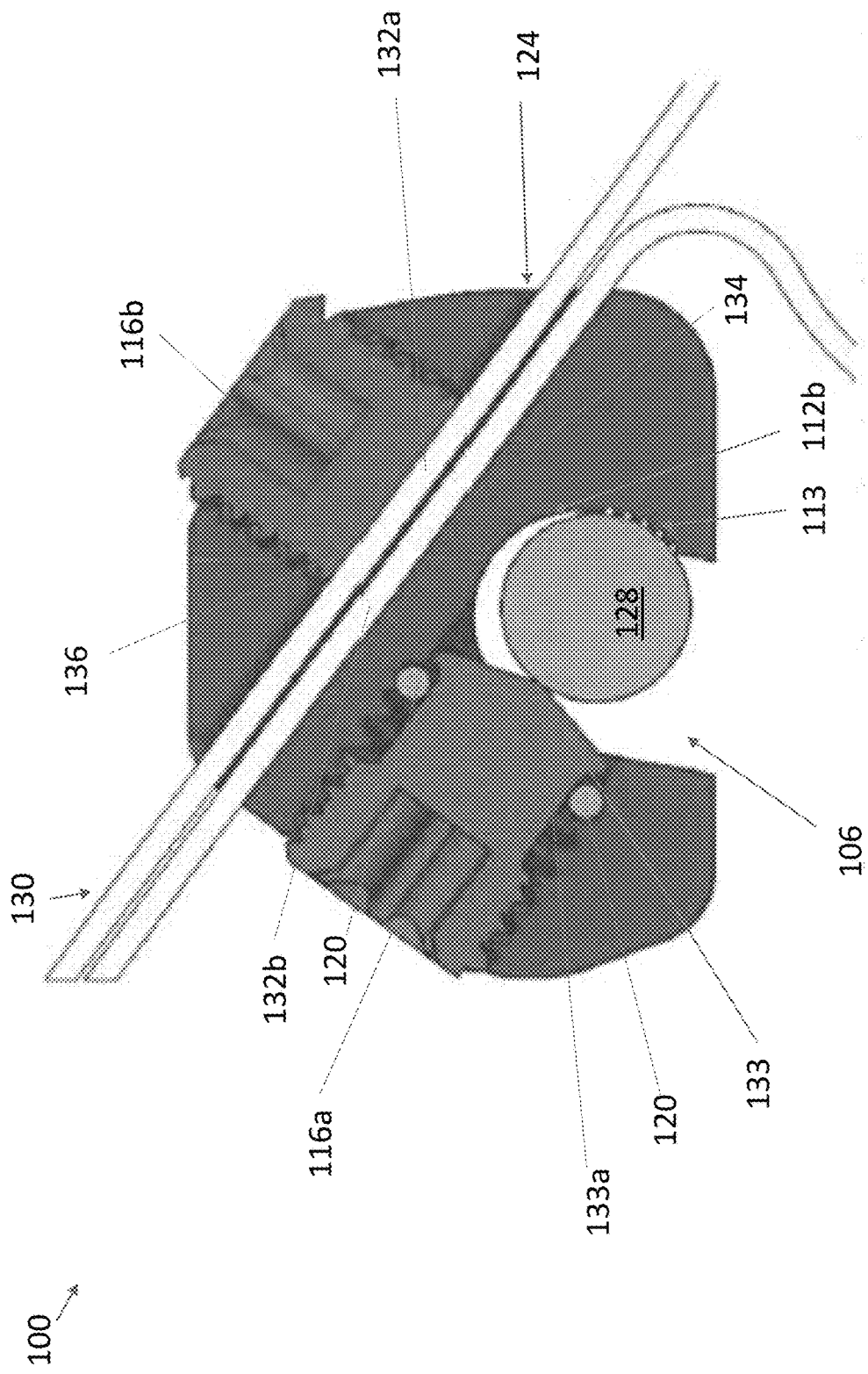
FIG. 4 is a cross-section of FIG. 3.

FIG. 4 illustrates a cross-section, of the clamp 100 of FIG. 3, taken along the dashed line extending between B and B' (as shown on FIG. 3). As shown on FIG. 4, the first clamping mechanism 116a may be tightened or moved forward away from the pins 120 and toward the spinal rod 128. A distal end 133 of the first clamping mechanism 116a may include a protrusion 133a that contacts the spinal rod 128. Upon tightening, the spinal rod 128 is secured within the opening 106. That is, the spinal rod 128 is compressed between the tapered distal end 133 and the inner surface 112b, upon tightening. The inner surface 112b may include teeth or grooves 113 to assist with gripping and stabilizing the spinal rod 128 within the opening 106, as shown. The second clamping mechanism 116b may be tightened or moved forward to compress the portions 132a and 132b of the sublaminar band 130 within the passage 124, thereby securing the portions 132a and 132b between an inner surface 134 of the passage 124 and a distal end 136 of the second clamping mechanism 116b, as shown.

Figure 5:
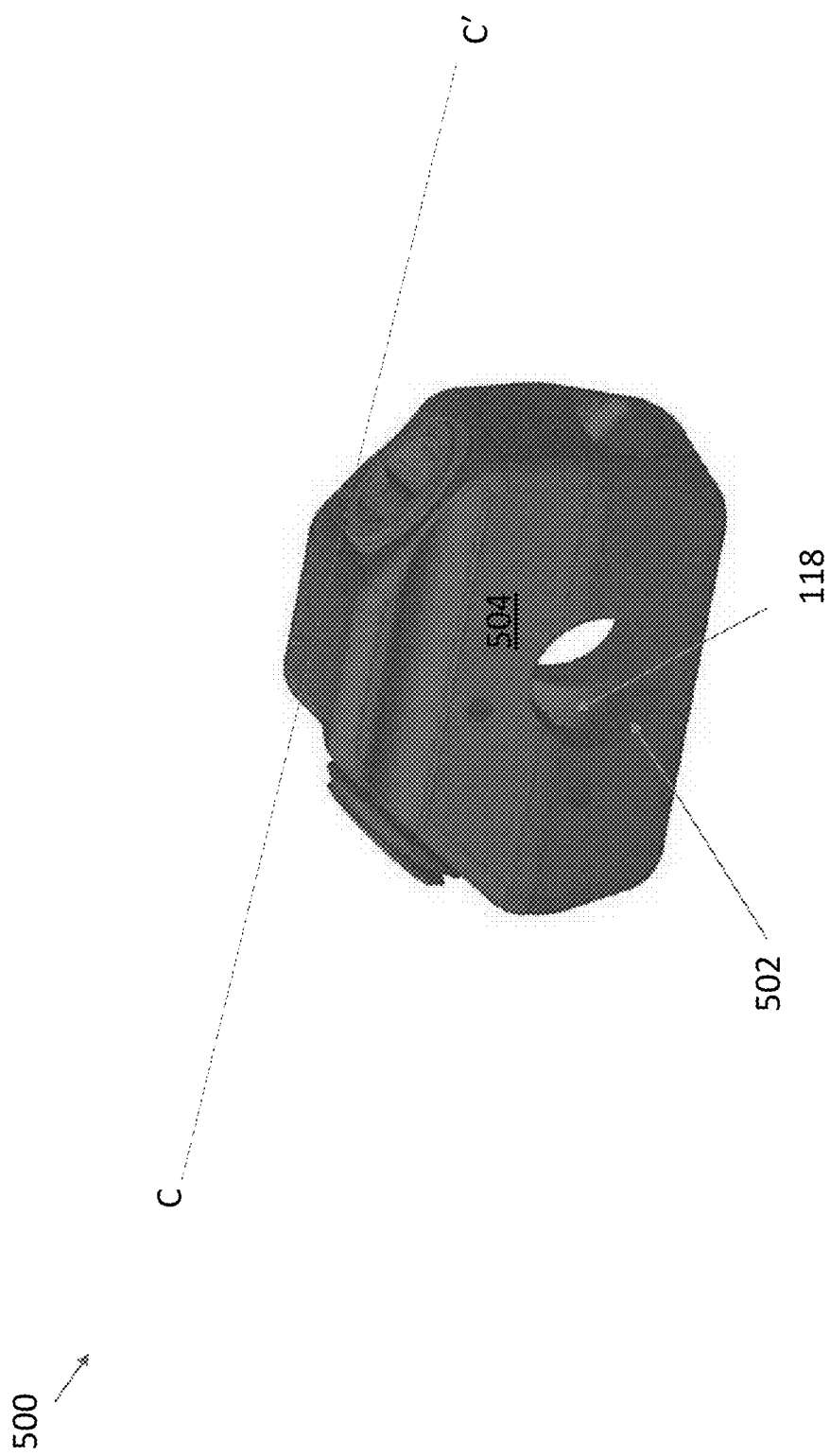
FIG. 5 illustrates a clamp in accordance with embodiments of the present disclosure.

FIG. 5 illustrates a clamp 500 in accordance with particular embodiments of the present disclosure. The clamp 500 may be similar to the clamp 100 (e.g., shown on FIGS. 1-4). However, instead of the opening 106, the clamp 500 includes an aperture 502 that is completely surrounded by a body 504 of the clamp 500, as shown. The aperture 502 is in fluid communication with the passage 118.

Figure 6:
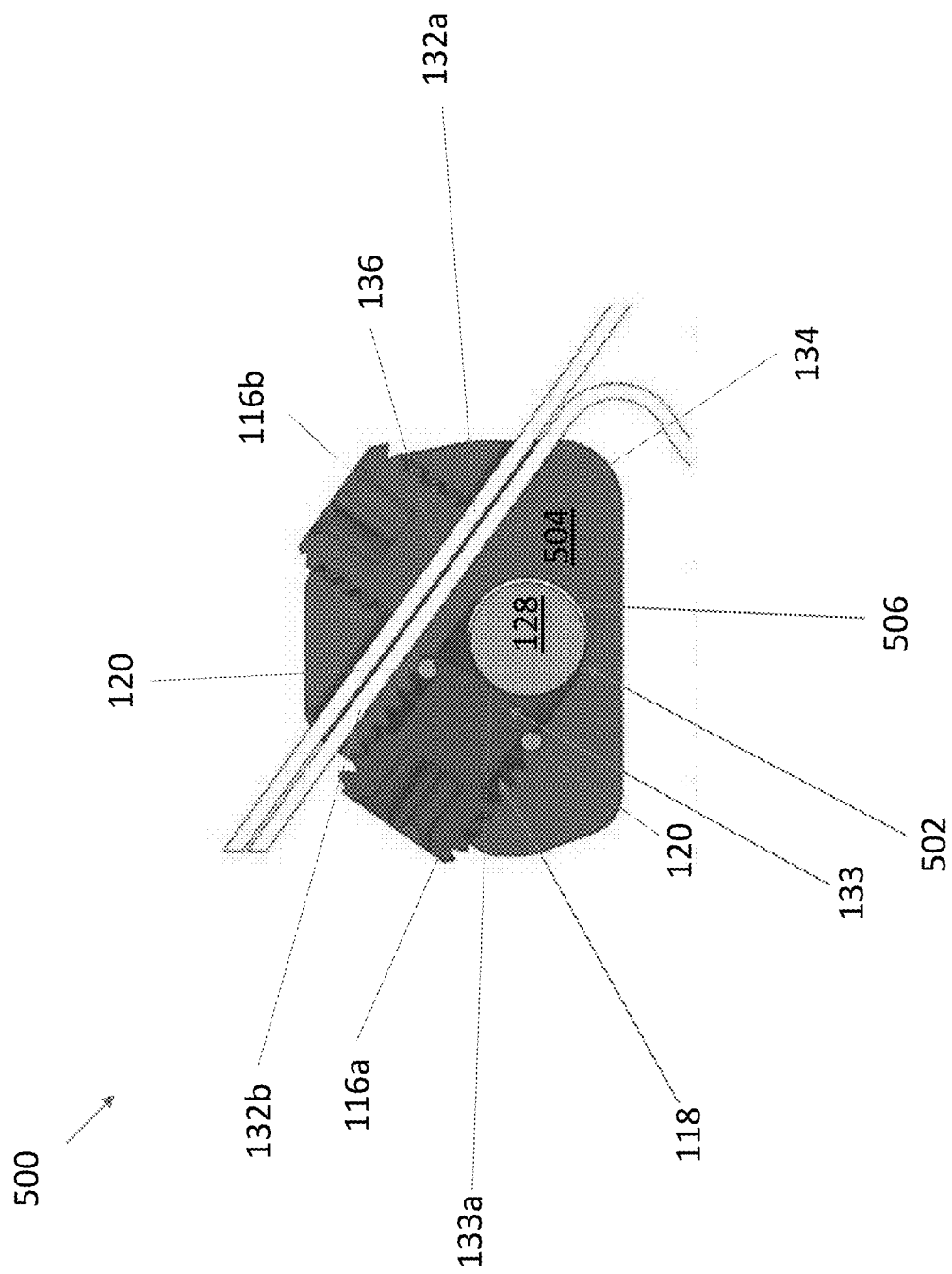
FIG. 6 is a cross-section of FIG. 5.

FIG. 6 illustrates a cross-section of the clamp 500 of FIG. 5 taken along the dashed line extending between C and C' (as shown on FIG. 5). As shown on FIG. 6, the first clamping mechanism 116a may be tightened or moved forward away from the pins 120 and toward the spinal rod 128. A distal end 133 of the first clamping mechanism 116a may include a protrusion 133a that contacts the spinal rod 128 thereby securing the spinal rod 128 within the opening 106, upon tightening. That is, upon tightening, the spinal rod 128 is compressed between the distal end 133 and an inner surface 506 of the aperture 502. The second clamping mechanism 116b may be tightened or moved forward to compress the portions 132a and 132b of the sublaminar band 130 within the passage 124, thereby securing the portions 132a and 132b between an inner surface 134 of the passage 124 and a distal end 136 of the second clamping mechanism 116b, as shown.

Figure 7:
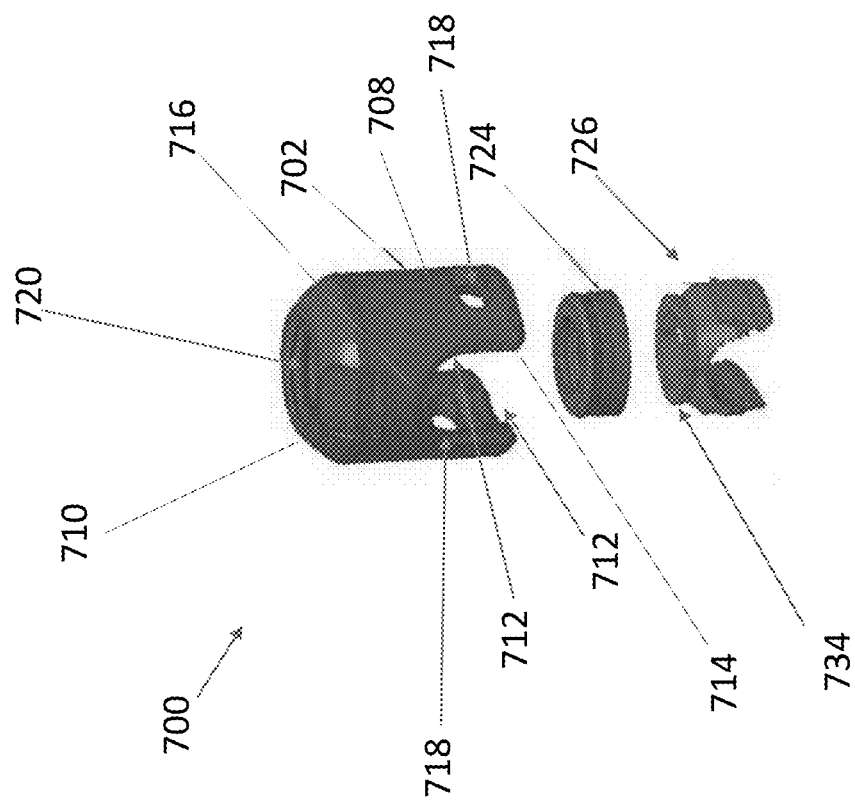
FIG. 7 illustrates a clamp system in accordance with embodiments of the present disclosure.

FIG. 7 illustrates a clamp system 700 in accordance with particular embodiments of the present disclosure. The clamp system 700 may include a tulip 702. The tulip 702 may resemble a bullet with a hollow interior. The tulip 702 may include a portion 708 that may be hollow and extends from a nose portion 710, as shown. The portion 708 may include openings 712 on opposing sides of the tulip 702, as shown. In certain embodiments, the openings 712 may resemble arches to correspond with a curvature of a spinal rod that may be positioned within the openings 712. The openings 712 may extend from a distal end 714 to (or at least partially through) a central portion 716 of the tulip 702, as shown. The portion 708 may include slots 718 positioned on an end of the tulip 702 that is opposite to the nose portion 710.

A passage 720 may extend centrally and longitudinally from and through the nose portion 710 through the tulip 702. The passage 720 may be in fluid communication with the openings 712 and the slots 718, as shown.

The clamp system 700 may further include a saddle 724 and a clamp 726 that are disposed within the tulip 702. The saddle 724 and the clamp 726 may be coupled together to form a locking mechanism 727, as shown on FIG. 8.

FIG. 8 is a perspective view of the locking mechanism 727 in accordance with particular embodiments of the present disclosure. As shown, the saddle 724 may be of a cylindrical shape and may include a groove 728 extending along a circumference of the saddle 724, as shown. The groove 728 may be positioned between ridges 730a and 730b which also extend circumferentially about the saddle 724, as shown. A passage 729 may be disposed at the center of the locking mechanism 727, as shown.

FIG. 9 is a cross-section of FIG. 8 taken along the dashed line extending between D and D' (as shown on FIG. 8). As shown on FIG. 9, the clamp 726 may include a first portion 732a and a second portion 732b which may be placed adjacent to each other to form a ring 734, as best shown on FIG. 7. The passage 729 may extend through the saddle 724 and the ring 734. The ring 734 may be positioned within a groove 736 that extends internally along an internal circumference of the saddle 724. The saddle 724 may also include ramps 738 extending along an outer edge of the saddle 724 to facilitate installation or coupling of the clamp 726 to the saddle 724. The clamp 726 may also include ridges 740 positioned along an internal surface of an opening 742 formed by the portions 732a and 732b.

Figure 10:
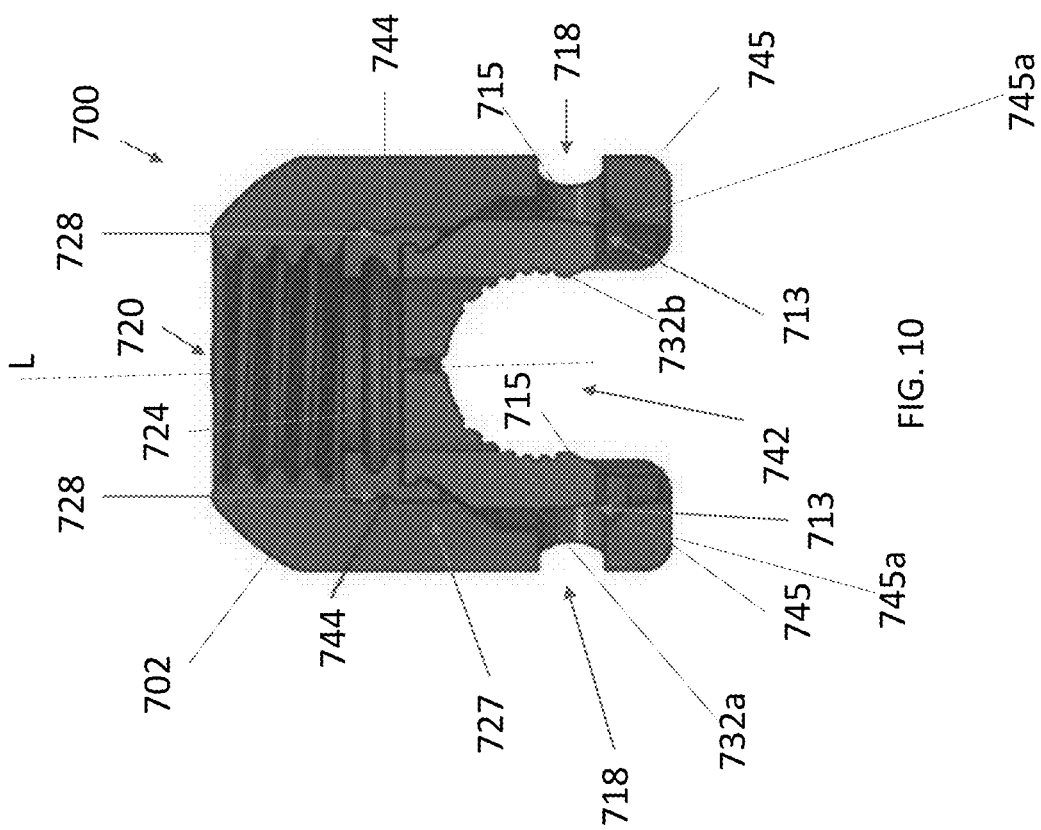
FIG. 10 is a cross-section of the clamp system of FIG. 7 in an assembled configuration in accordance with embodiments of the present disclosure.

FIG. 10 illustrates a cross-section of the clamp system 700 including the locking mechanism 727 positioned within the tulip 702 in a first configuration or unlocked position, in accordance with particular embodiments of the present disclosure. That is, the position of the locking mechanism 727 may be adjustable. In some embodiments, the locking mechanism 727 may be move axially in a direction of a longitudinal axis L. As shown, the passage 720 may be threaded and may include protrusion 744 that extends into the groove 728 of the saddle 724 to secure the locking mechanism within the tulip 702. As shown, the protrusion 744 is between and adjacent to the ridges 730a and 730b. In this unlocked position, a space 713 is formed between the distal ends 745 and distal ends 715 of the portions 732a and 732b, as shown. The space 713 may be in fluid communication with the opening 742 and the slots 718 of the tulip 702. The space 713 can allow placement or installation of a sublaminar band (e.g., sublaminar band 130 as shown on FIGS. 13 and 14) within the clamp system 700. The opening 742 may include a profile that aligns with and corresponds to the shape the opening 712 shown on FIG. 7 to allow reception and securing of a spinal rod (e.g., spinal rod 128 as shown on FIGS. 13 and 14).

Figure 11:
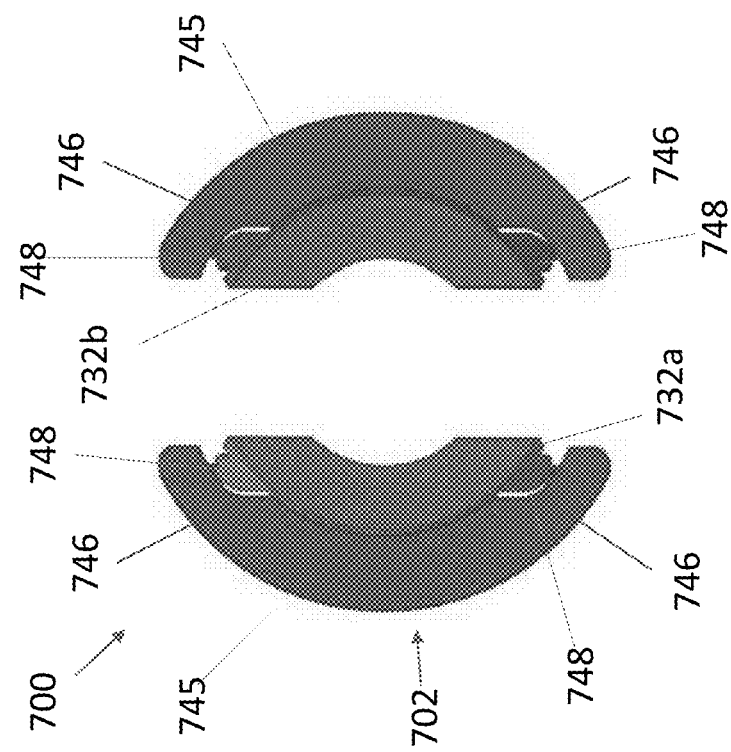
FIG. 11 is a bottom view of a tulip and a clamp of the clamp system of FIG. 7, in accordance with embodiments of the present disclosure.

FIG. 11 is a bottom view of the portions 732a and 732b positioned within the tulip 702 in accordance with particular embodiments of the present disclosure. As shown, the inner surfaces of distal ends 745 of the tulip 702 may include recesses 746 to complement, mate, or correspond with ridges 748 that protrude outward from the portions 732a and 732b that may be positioned between the distal ends 745 and the portions 732a and 732b. The distal ends 745 may include tapered regions 745a to force the distal ends 715 inward thereby securing the sublaminar band, upon depression of the locking mechanism 727. Also, the tapered regions 745a may retain the locking mechanism 727 within the tulip 702.

Figure 12:
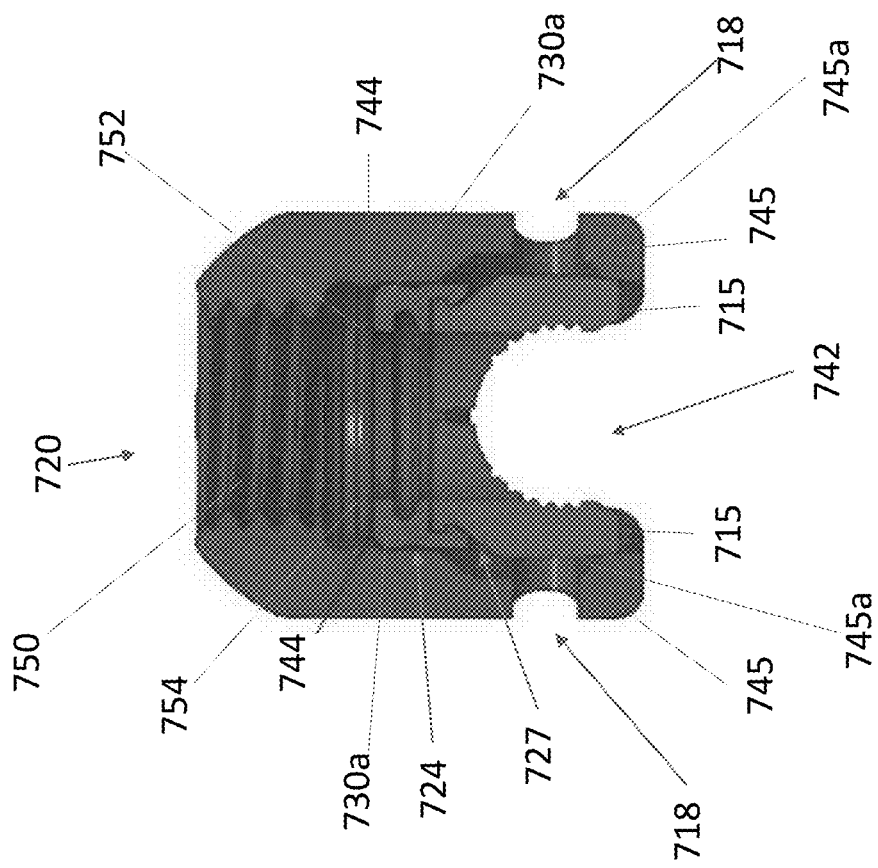
FIG. 12 is a cross-section of a locking mechanism in a locked position in accordance with embodiments of the present disclosure.

FIG. 12 illustrates a cross-section of the locking mechanism 727 positioned within the tulip 702 in a second configuration or locked position, in accordance with particular embodiments of the present disclosure. As shown, the passage 720 includes a first portion 750 (e.g., a threaded portion) and a second portion 752 (e.g., a chamber). In certain embodiments, the second portion 752 does not include threads and may have an inner diameter that is larger than an inner diameter of the first portion 750. The saddle 724 may have an outer diameter that is larger than an inner diameter of the first portion 750. The protrusion 744 may be positioned within the second portion 752. In the second position, the second portion 752 is not completely occupied resulting in a gap 754 positioned between the ridge 730a and the first portion 750. In comparison, with reference back to FIG. 10, in the first position, the second portion 752 is completely occupied with no gap 754. As shown in the locked position, the space 713 is reduced thereby holding or locking a sublaminar band in place between the distal ends 715 and the distal ends 745.

Figure 13B:
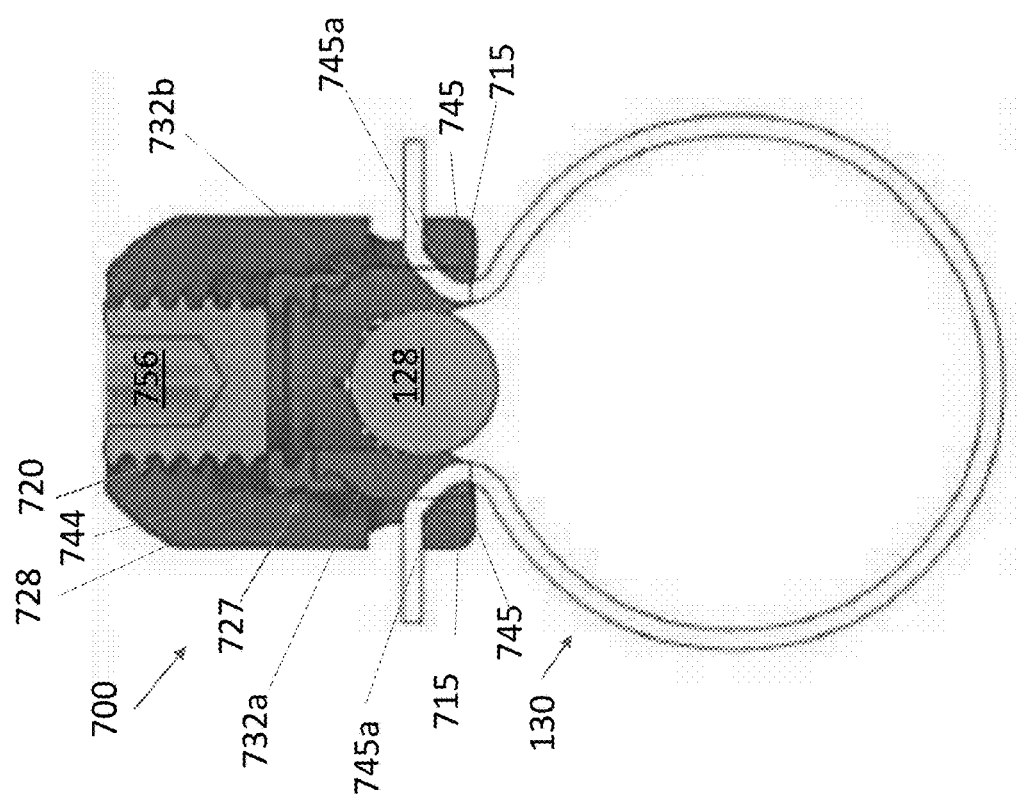
FIG. 13B is a cross-section of the clamp system of FIG. 13A in a locked position, in accordance with embodiments of the present disclosure.
Figure 13A:
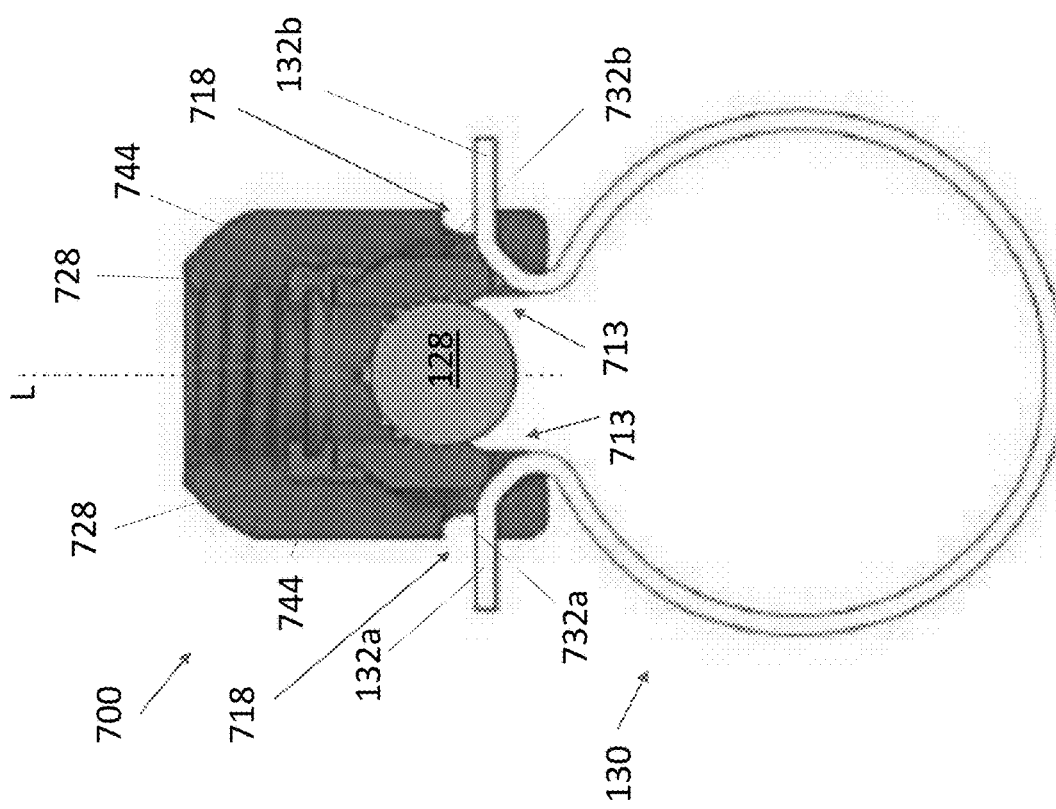
FIG. 13A is a cross-section of a clamp system with a sublaminar band in an unlocked position, in accordance with embodiments of the present disclosure.

FIG. 13A illustrates a cross-section of the clamp system 700, with the sublaminar band 130, in the unlocked position, in accordance with particular embodiments of the present disclosure. As shown, the portions 132a and 132b of the sublaminar band 130 may be positioned through the space 713 and the slots 718, as shown. The spinal rod 128 may be disposed between the portions 732a and 732b, as shown. The spinal rod 128 may extend in a lateral direction relative to a longitudinal axis L of the clamp system 700, as shown. In the unlocked position, the protrusion 744 may be aligned and positioned within with the groove 728.

FIG. 13B illustrates a cross-section of the clamp system 700, with the sublaminar band 130, in the locked position, in accordance with particular embodiments of the present disclosure. As shown, the space 713 is reduced thereby holding or locking a sublaminar band in place between the distal ends 715 and the distal ends 745. As previously noted, the tapered regions 745a cause the distal ends 715 to move inward as the locking mechanism 727 is moved or translated toward the sublaminar band 130. This inward movement secures or locks the sublaminar band 130 in place, as shown. In the locked position, the protrusion 744 is not aligned with the groove 728 and is positioned outside (e.g., above the groove 728) of and adjacent to the groove 728, as shown.

In certain embodiments, the clamp system 700 may further include a threaded locking cap 756. The locking mechanism 727 may be moved, translated, or locked into place with the threaded locking cap 756 that may be removably disposed (e.g., a separate piece) within the passage 720, as shown. The threaded locking cap 756 may be rotated thereby moving or shifting the locking mechanism 727 toward the spinal rod 128, thereby securing the spinal rod 128 and the sublaminar band 130, as shown. In other words, the threaded locking cap 756 may be rotated to translate the locking mechanism 727 from the unlocked position to the locked position, as described herein.

Figure 14B:
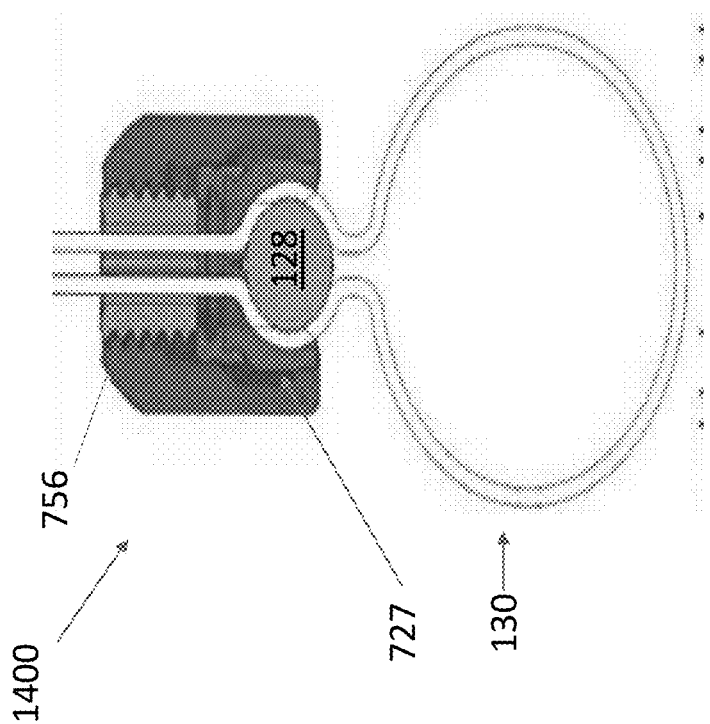
FIG. 14B is a cross-section of the clamp system of FIG. 14A in a locked position, in accordance with embodiments of the present disclosure.
Figure 14A:
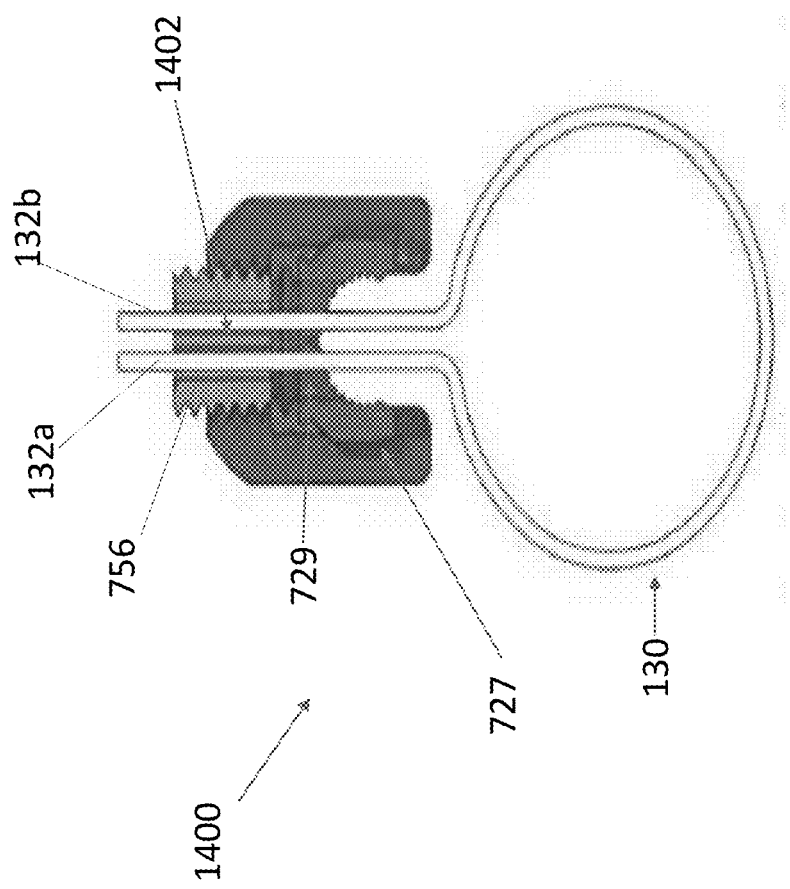
FIG. 14A is a cross-section of a clamp system with a sublaminar band in an unlocked position, in accordance with embodiments of the present disclosure.

FIG. 14A illustrates a cross-section of a clamp system 1400 in an unlocked position in accordance with particular embodiments of the present disclosure. The clamp system 1400 is similar to the clamp system 700 (e.g., shown on FIGS. 7 to 13B). However, placement of the sublaminar band 130 differs from previously described configurations. As shown, the sublaminar band 130 may be positioned to extend through a passage or central cannulation 1402 of the threaded locking cap 756 and through the passage 729 of the locking mechanism 727.

FIG. 14B illustrates a cross-section of the clamp system 1400 in a locked position in accordance with particular embodiments of the present disclosure. As shown, as the locking mechanism 727 is translated (e.g., moved toward the spinal rod 128) into a locked position with the threaded locking cap 756, the sublaminar band 130 may be squeezed and secured between the spinal rod 128 and the locking mechanism 727, as shown.

Figure 15B:
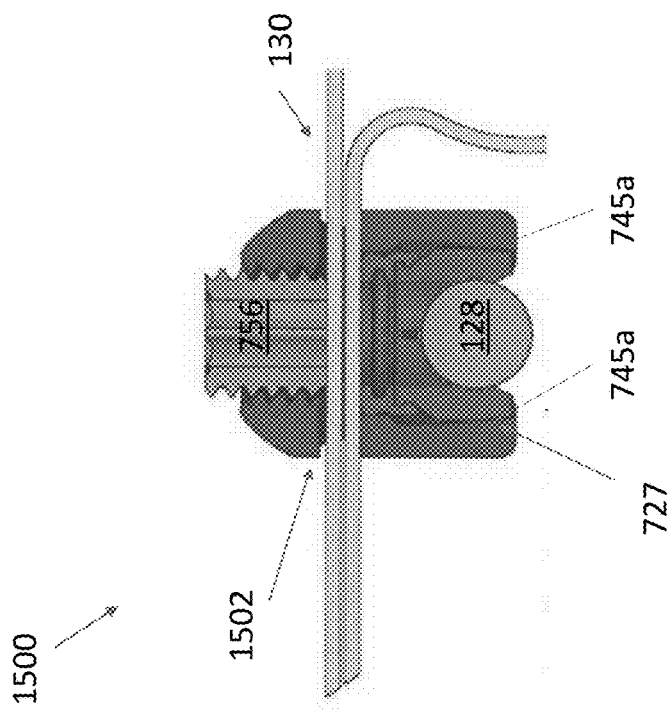
FIG. 15B is a cross-section of the clamp system of FIG. 15A in a locked position, in accordance with embodiments of the present disclosure.
Figure 15A:
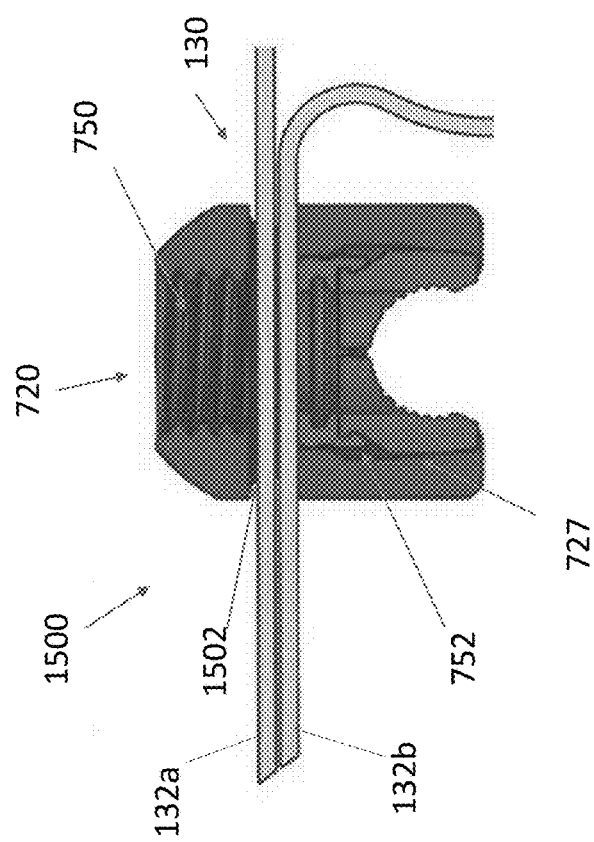
FIG. 15A is a cross-section of a clamp system with a sublaminar band in an unlocked position, in accordance with embodiments of the present disclosure.

FIG. 15A illustrates a cross-section of a clamp system 1500 in an unlocked position in accordance with particular embodiments of the present disclosure. The clamp system 1500 is similar to the clamp system 1400 (e.g., shown on FIGS. 14A and 14B). However, placement of the sublaminar band 130 differs from previously described configurations. As shown, the portions 132a and 32b of the sublaminar band 130 are stacked and positioned to extend through a passage 1502 that extends between the first portion 750 and the second portion 752 of the passage 720.

FIG. 15B illustrates a cross-section of the clamp system 1500 in a locked position in accordance with particular embodiments of the present disclosure. As shown, as the locking mechanism 727 is translated (e.g., moved toward the spinal rod 128) into a locked position with the threaded locking cap 756, the sublaminar band 130 may be squeezed and secured between the locking mechanism 727 and the threaded locking cap 756, as shown. Also, the spinal rod 128 may be locked into place due to the tapered regions 745a as described herein.

Figure 16:
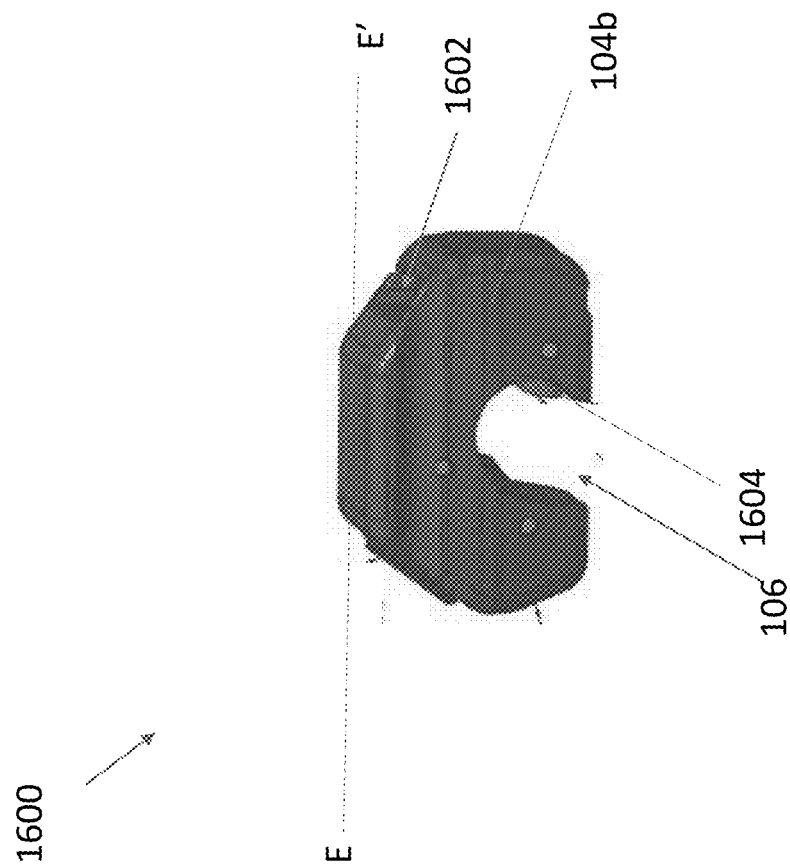
FIG. 16 illustrates a clamp in accordance with embodiments of the present disclosure.

FIG. 16 illustrates a clamp 1600 that is similar to the clamp 100 (e.g., shown on FIG. 1). However, placement of the sublaminar band differs from previously described configurations. As shown, the clamp 1600 includes a passage 1602 extending through the portion 104b. The clamp 1600 also includes a sliding or moveable member ("member") 1604 to secure the sublaminar band within the passage 1602. The member 1604 may be elongated and rigid, and may be disposed between the opening 106 and the passage 1602, as shown.

Figure 17B:
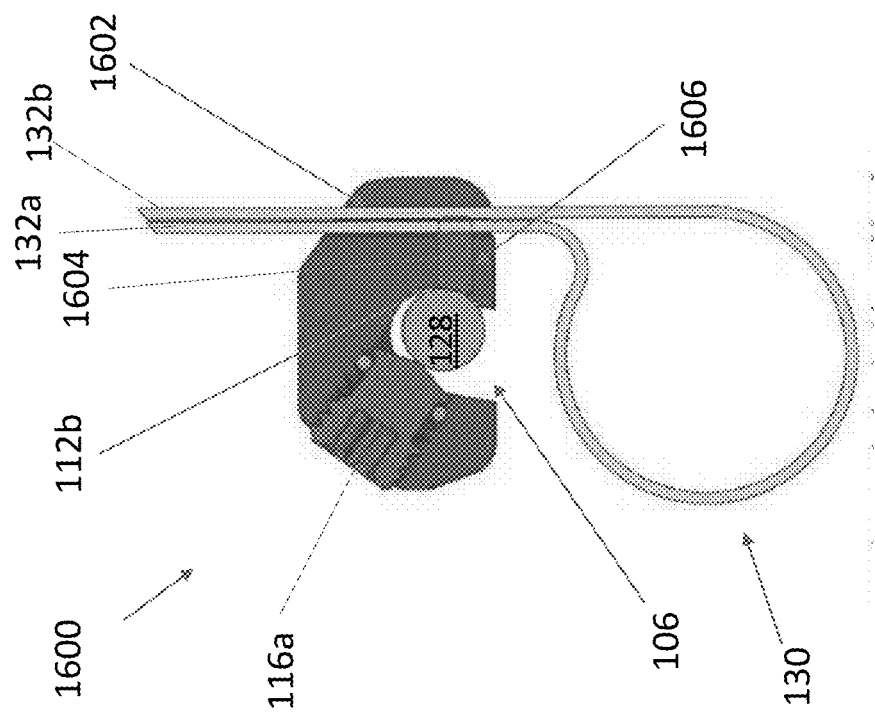
FIG. 17B is a cross-section of the clamp of FIG. 16 with a sublaminar band in a locked position, in accordance with embodiments of the present disclosure.
Figure 17A:
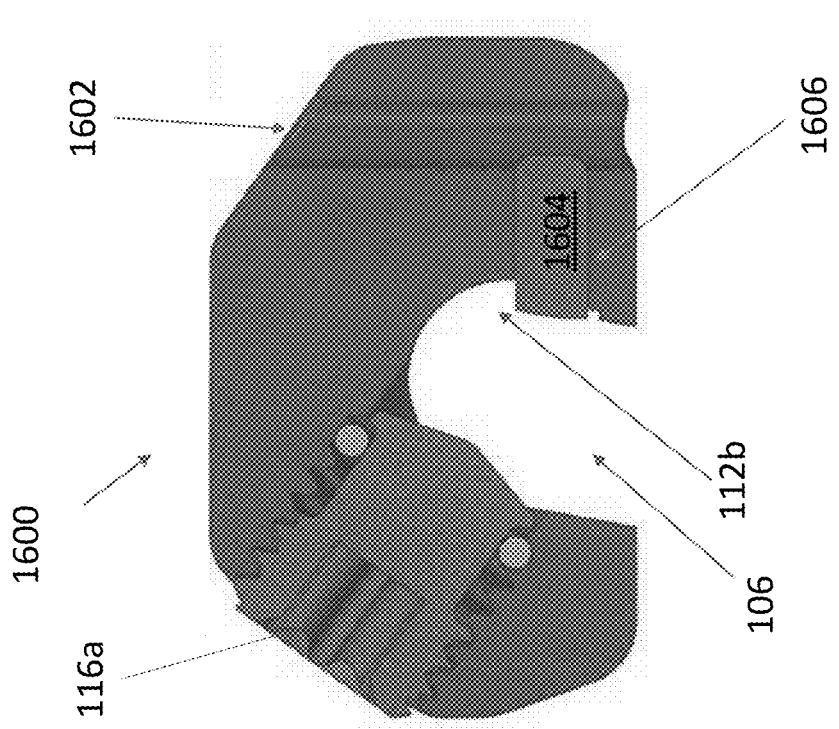
FIG. 17A is a cross-section of FIG. 16.

FIG. 17A illustrates a cross-section of the clamp 1600 taken along the dashed line extending between E and E' (as shown on FIG. 16). As shown on FIG. 17A, the passage 1602 is in fluid communication with the passage 1606 that contains the member 1604. The passage 1606 may intersect the passage 1602 orthogonally. As shown, the passage 1604 extends through the inner surface 112b.

FIG. 17B illustrates another cross-section of the clamp 1600 including the sublaminar band 130 and the spinal rod 128, in accordance with particular embodiments of the present disclosure. As shown, the sublaminar band 130 may extend through the passage 1602. The sublaminar band 130 may be folded or curved and may include portions 132a and 132b which are stacked upon each other, as shown. The locking mechanism 116a may be tightened to move the spinal rod 128 toward the member 1604. This causes the member 1604 to move toward the passage 1602 thereby compressing and securing the sublaminar band 130, as shown. Additionally, the spinal rod 128 may be secured between a portion of the member 1604 and the locking mechanism 116a, as shown.

Figure 18:
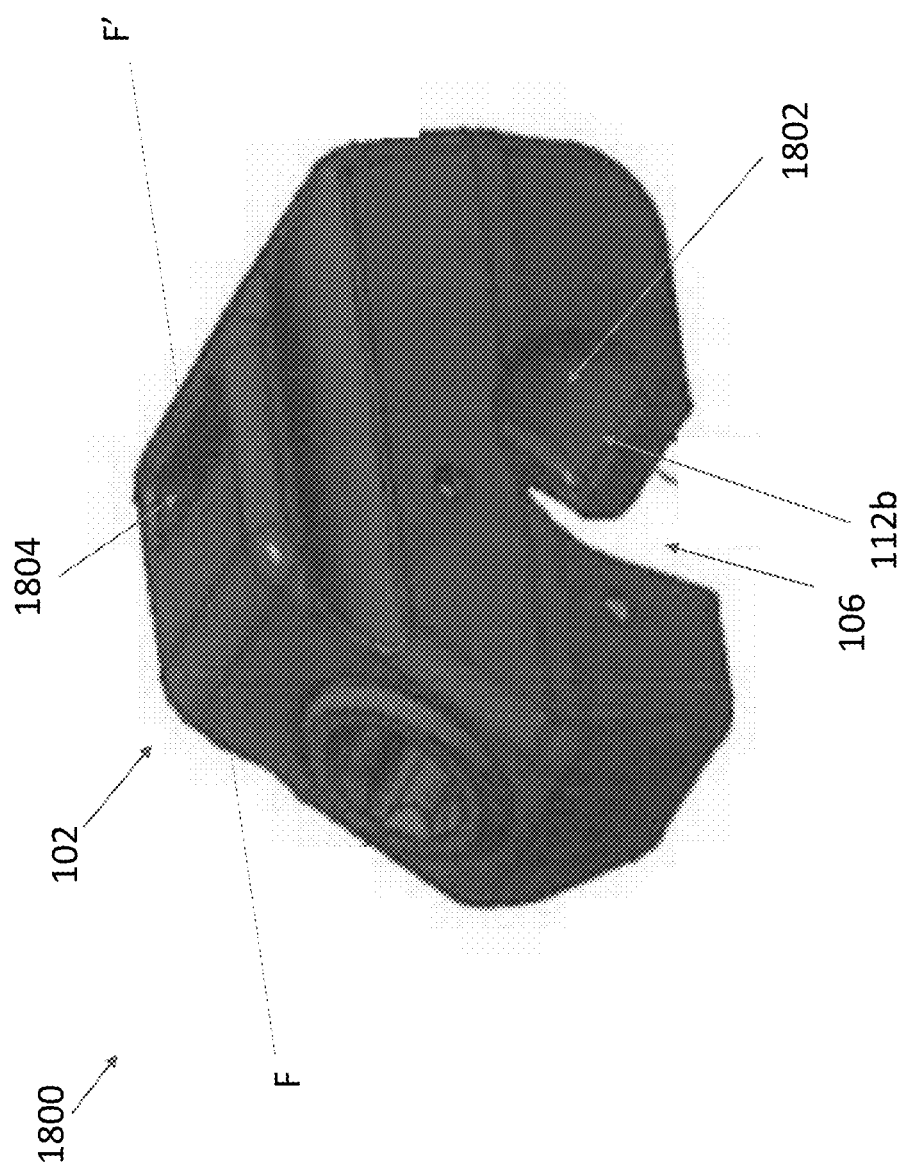
FIG. 18 illustrates a clamp in accordance with embodiments of the present disclosure.

FIG. 18 illustrates a clamp 1800 that is similar to the clamp 1600 (e.g., shown on FIG. 16), in accordance with particular embodiments of the present disclosure. However, placement of the sublaminar band differs from previously described configurations. As shown, the clamp 1800 includes a groove 1802 positioned on the inner surface 112b. The clamp 1800 also includes a passage 1804 extending from the nose portion 102 to the opening 106, as shown.

Figure 19B:
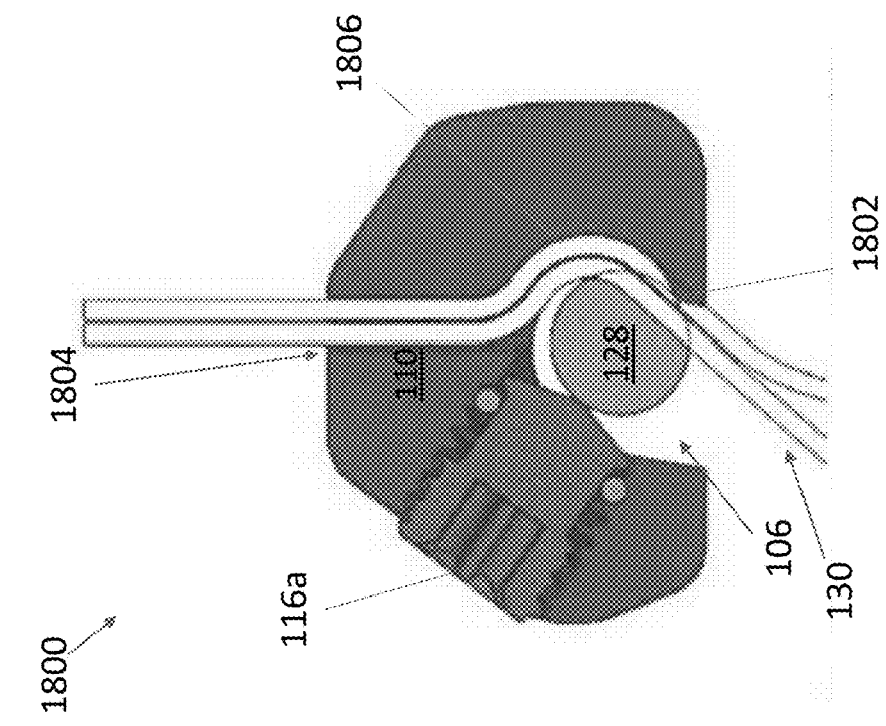
FIG. 19B is a cross-section of the clamp of FIG. 18 with a sublaminar band in a locked position, in accordance with embodiments of the present disclosure.
Figure 19A:
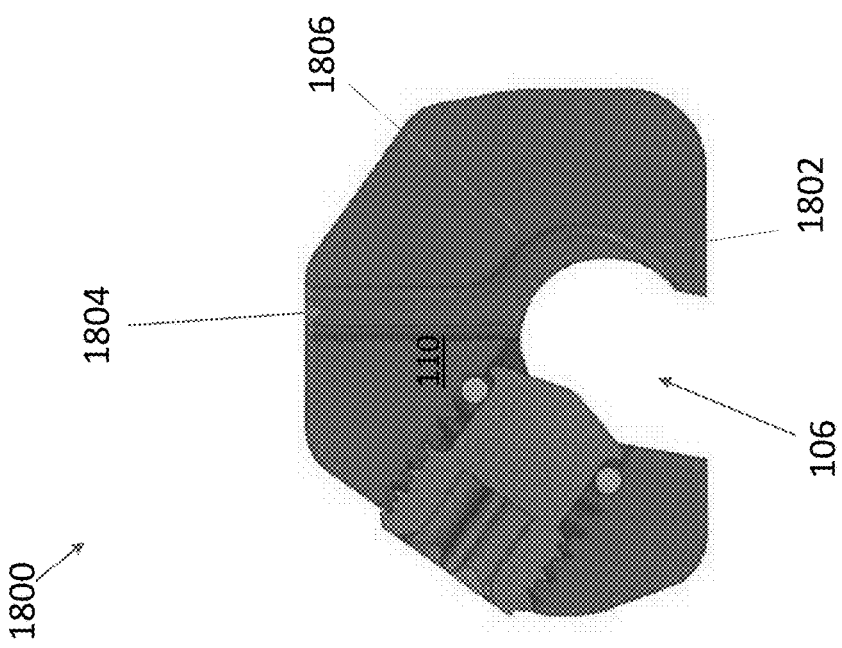
FIG. 19A is a cross-section of FIG. 18.

FIG. 19A illustrates a cross-section of the clamp 1800 taken along the dashed line extending between F and F' (as shown on FIG. 18). As shown on FIG. 19A, the groove 1802 may extend along the passage 1804, as shown. The passage 1804 may include a curve 1806 that corresponds with the shape of the spinal rod 128, as shown on FIG. 19B.

FIG. 19B illustrates another cross-section of the clamp 1800 including the sublaminar band 130 and the spinal rod 128, in accordance with particular embodiments of the present disclosure. The groove 1802 can stabilize the sublaminar band 130 within the passage 1804 and against the curve 1806. As shown, the locking mechanism 116a may be tightened to move the spinal rod 128 toward the sublaminar band 130. The spinal rod 128 may be secured between the locking mechanism 116a and the sublaminar band 130, as shown. The sublaminar band 130 may be secured between the spinal rod 128 and the curve 1806 of the passage 1804, as shown.

Figure 20:
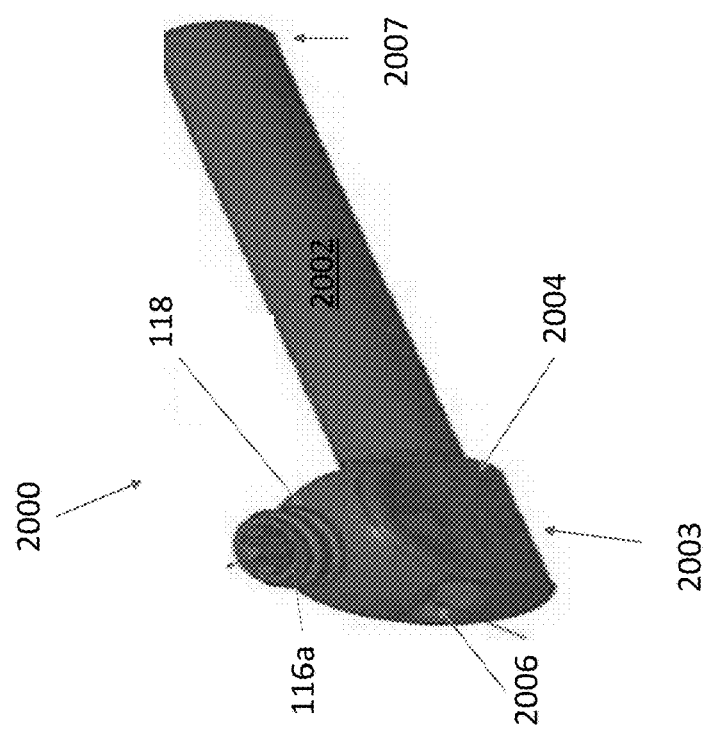
FIG. 20 illustrates a spinal rod integrated with a clamp, in accordance with embodiments of the present disclosure.

FIG. 20 illustrates a spinal rod 2000 in accordance with embodiments of the present disclosure. The spinal rod 2000 may be similar to the spinal rod 128 (e.g., shown on FIGS. 3, 4, 6, 13A, 13B, 14B, 15B, 17B) as described herein. The spinal rod 2000 may include an elongated portion 2002 that is integrated with a clamp 2003 that may be similar to previously described clamps.

The clamp 2003 may include a body 2004 and may include the locking mechanism 116a (and the passage 118 as shown on FIG. 1, for example). The clamp 2003 may be disposed on an end of the elongated portion 2002, as shown. The clamp 2003 may include a passage 2006 that extends through the body 2004 in a direction toward an end 2007 of the elongated portion 2002 that is opposite to the clamp 2003. The passage 2006 may be in fluid communication with the passage 118.

Figure 21:
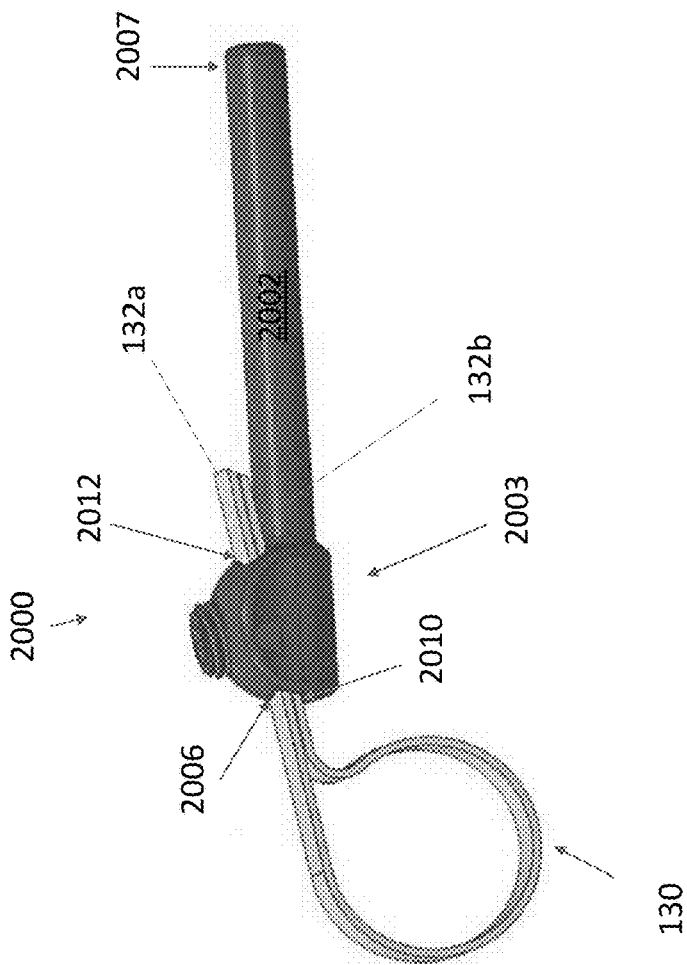
FIG. 21 illustrates a sublaminar band secured to the clamp of FIG. 20, in accordance with embodiments of the present disclosure.

FIG. 21 illustrates the spinal rod 2000 with the sublaminar band 130, in accordance with particular embodiments of the present disclosure. As shown, the sublaminar band 130 may extend through the passage 2006. The passage 2006 may include an opening 2010 at a distal end of the spinal rod 2000, as shown. Additionally, the passage 2006 may include an opening 2012 at a section of the clamp 2003 that is adjacent to the elongated portion 2002, as shown. The portions 132a and 132b of the sublaminar band 130 may extend adjacent to the elongated portion 2002, as shown. The locking mechanism 116a may be tightened thereby securing the sublaminar band 130 within the passage 2006.

Figure 22:
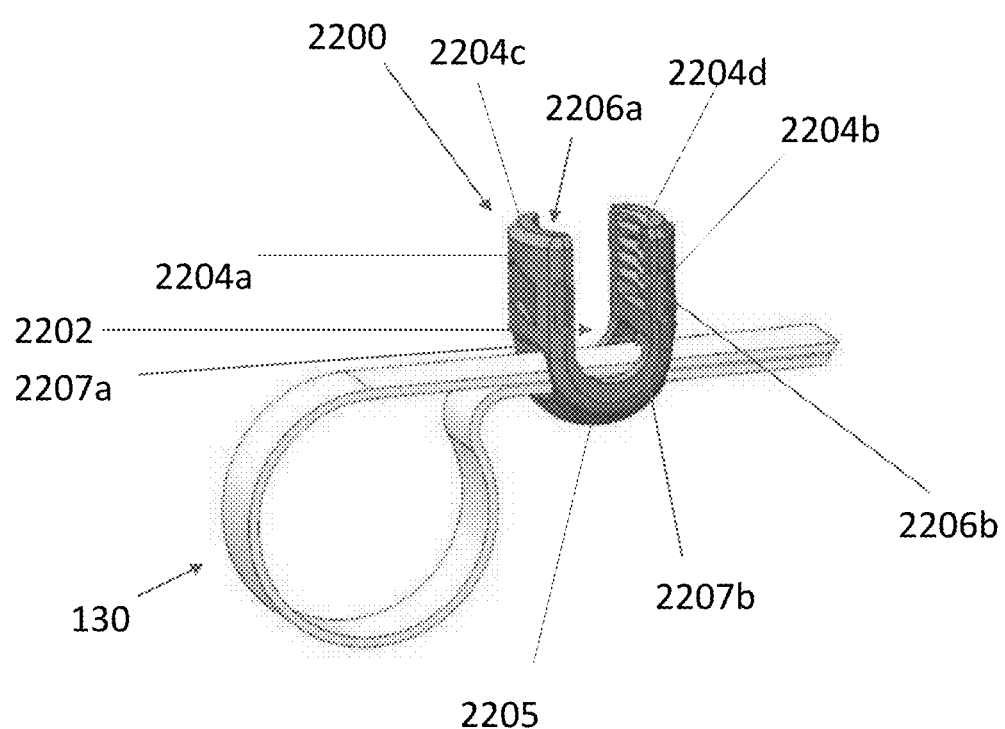
FIG. 22 illustrates a clamp in accordance with embodiments of the present disclosure.

FIG. 22 illustrates a clamp 2200 in accordance with particular embodiments of the present disclosure. As shown, the clamp 2200 may include an opening 2202 situated between portions 2204a and 2204b. A curved portion 2205 may be disposed between the portions 2204a and 2204b, as shown. In certain embodiments, the opening 2202 may extend from the curved portion 2205 to distal ends 2204b and 2204c of the portions 2204a and 2204b, as shown. Inner surfaces 2206a and 2206b of the portions 2204a and 2204b may be threaded. The portions 2204a and 2204b may include apertures 2207a and 2207b. The apertures 2207a and 2207b may be in fluid communication with the opening 2202, as shown. The sublaminar band 130 may extend through the apertures 2207a, 2207b, and the opening 2202, as shown.

Figure 23:
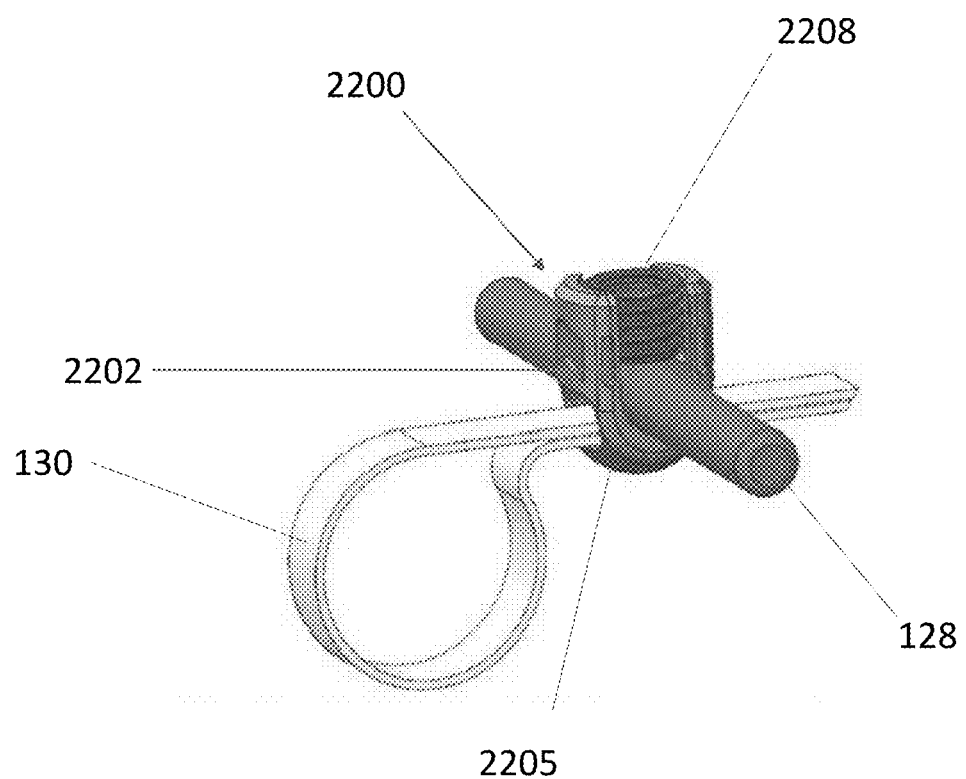
FIG. 23 illustrates the clamp of FIG. 22 secured to a spinal rod in accordance with embodiments of the present disclosure.

FIG. 23 illustrates the clamp 2200 secured to the spinal rod 128 in accordance with particular embodiments of the present disclosure. As shown, the rod 128 may extend through the opening 2202. The spinal rod 128 may be disposed between the sublaminar band 130 and a set screw or locking cap 2208 that may be inserted between the portions 2204a and 2204b, as shown. The locking cap 2208 may be threaded and may be tightened to secure the spinal rod 128 and the sublaminar band within the opening 2202, as shown. The sublaminar band 130 may be secured between the curved portion 2205 and the spinal rod 128. And the spinal rod 128 may be secured between the locking cap 2208 and the sublaminar band 130, as shown. In certain embodiments, the spinal rod 128 may be positioned orthogonal to the sublaminar band 130.

Figure 24:
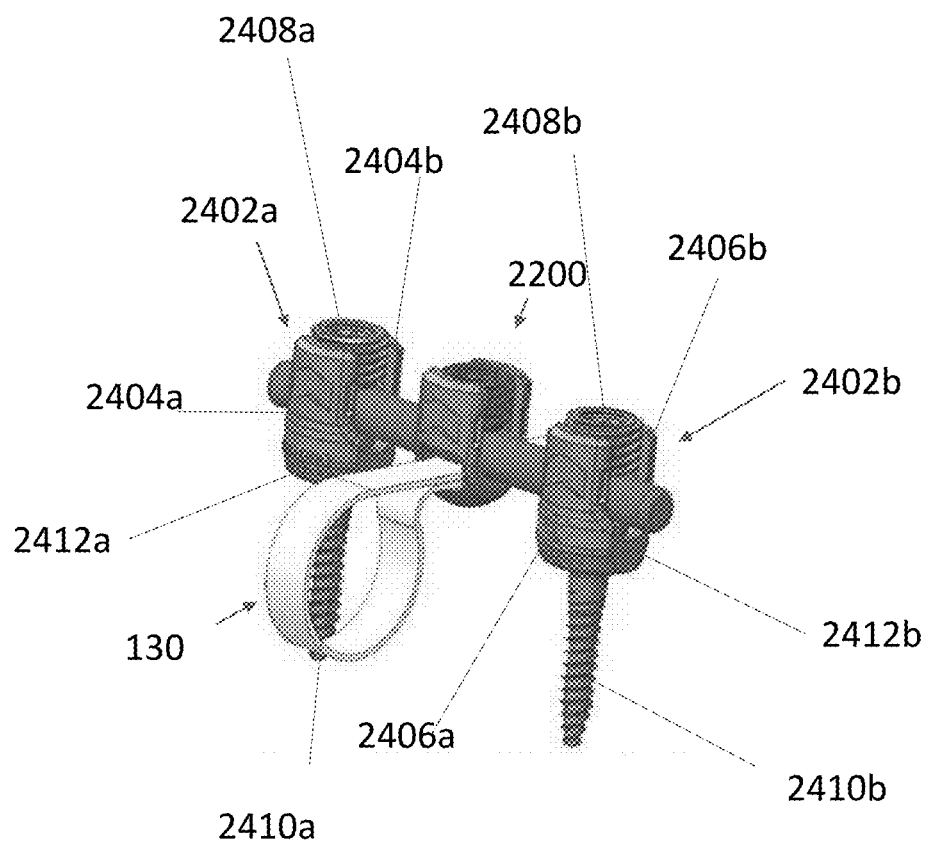
FIG. 24 illustrates the clamp of FIG. 22 positioned between pedicle screw assemblies, in accordance with embodiments of the present disclosure.

FIG. 24 illustrates the clamp 2200 positioned between pedicle screw assemblies 2402a and 2402b, in accordance with particular embodiments of the present disclosure. The pedicle screw assemblies 2402a and 2402b may include similar components to that of the clamp 2200. For example, the pedicle screw assemblies 2402a and 2402b may include clamps 2402a and 2402b that are similar to the clamp 2200, as described herein. The clamps 2402a and 2402b may include portions 2404a, 2404b, and 2406a, 2406b, respectively, that are similar to the portions 2204a and 2204b. Also, locking caps 2408a and 2408b may be disposed between the portions 2404a, 2404b, and 2406a, 2406b, respectively. The locking caps 2408a and 2408b may be similar to the locking cap 2208.

Pedicle screws 2410a and 2410b may extend through curved portions 2412a and 2412b, as shown, for attachment into a bone of a patient during a surgical procedure, for example. The curved portions 2412a and 2412b may be similar to the curved portion 2205.

FIG. 25A illustrates a clamp system 2500 in accordance with particular embodiments of the present disclosure. The clamp system 2500 may include first portion 2500a including a clamp 2501 that is similar to the clamp 2200 as shown on FIG. 22, for example. However, the clamp 2501 may include a passage 2502 that is in fluid communication with the opening 2202. The passage 2502 may be positioned within a base 2503, as shown. Portions 2505 and 2507 may extend from the base 2503. The base 2503 may be opposite to distal ends 2505a and 2505b of the portions 2505 and 2507, as shown. The first portion 2500a may extend in a direction of a longitudinal axis $L_1$.

The clamp system 2500 may further include the saddle 724 and the clamp 726 to form the locking mechanism 727, as previously described. In certain embodiments, the clamp 726 may be made of separate overlapping or interlocking portions 726a and 726b. The locking mechanism 727 may be secured within the passage 2502.

The clamp system 2500 may further include a second portion 2500b that may be coupled to the first portion 2500a. The second portion 2500b may include a body 2511 that may extend in a direction of a longitudinal axis $L_2$. In some embodiments, $L_2$ may be parallel to $L_1$. The second portion 2500b may include an aperture 2504 in fluid communication with an opening 2506, as shown. A screw 2508 may include a flange 2508a disposed adjacent to a threaded portion 2508b. The flange 2508a may be inserted through the opening 2506 and press-fitted into an aperture 2510 of a carriage 2512 thereby coupling the carriage 2512 to the screw 2508. In certain embodiments, a carriage assembly 2509 may include the carriage 2512 and the screw 2508. The carriage assembly 2509 may be retained in the second portion 2500b.

FIG. 25B illustrates the carriage assembly 2509 installed into the second portion 2500b, and also shows the locking mechanism 727 installed into the first portion 2500a, in accordance with particular embodiments of the present disclosure. In other words, the components of FIG. 25A are shown assembled in FIG. 25B, to form the clamp system 2500.

Figure 26B:
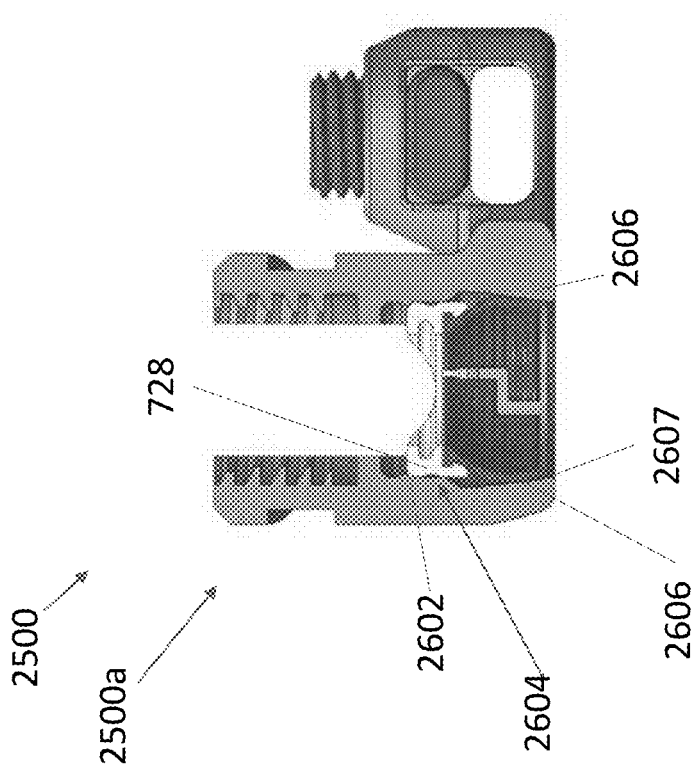
FIG. 26B is a cross-section of a first portion of the clamp system, as shown on FIG. 25B, in a locked position, in accordance with embodiments of the present disclosure.
Figure 26A:
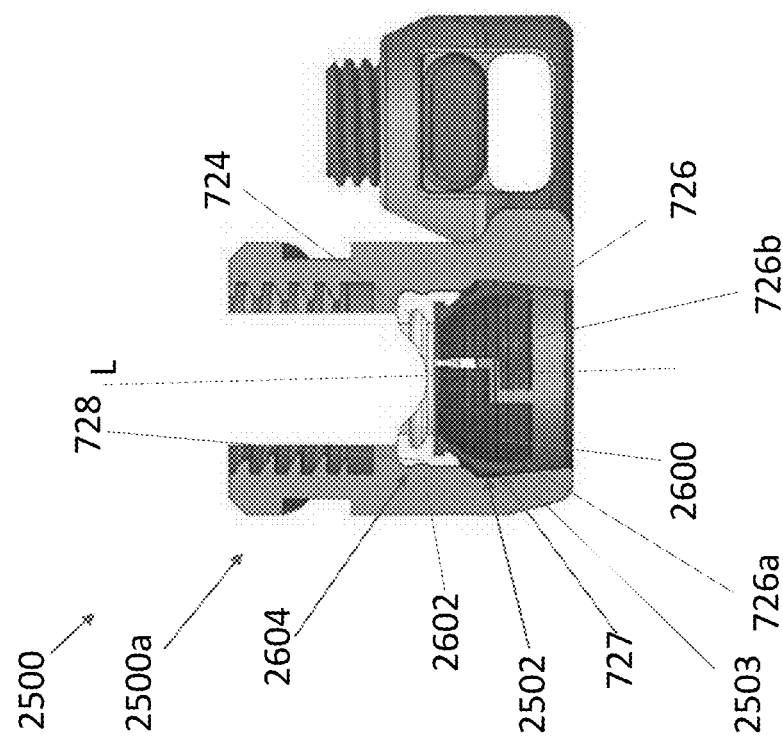
FIG. 26A is a cross-section of a first portion of the clamp system, as shown on FIG. 25B, in an unlocked position, in accordance with embodiments of the present disclosure.

FIG. 26A is a partial cross-section of the clamp system 2500 taken along the dashed line extending between G and G' (as shown on FIG. 25B). FIG. 26A illustrates the locking mechanism 727 in an unlocked position. The partial cross-section illustrates an inside of the first portion 2500a with the locking mechanism 727 disposed therein. As shown, the locking mechanism 727 is disposed within passage 2502. In certain embodiments, the clamp 726 may include an inner surface 2600 that is threaded to correspond with a head of a screw such as the pedicle screws 2410a and 2410b, shown on FIG. 24 for example. The passage 2502 may extend through the base 2503.

Protrusion 2602 of an inner surface 2604 of the passage 2502 may extend into the groove 728. The protrusion 2602 may be similar to the protrusion 744, shown on FIG. 10 for example. As shown, the locking mechanism 727 may be disposed within the passage 2502 and may move axially therein, in a direction of a longitudinal axis L.

FIG. 26B is a partial cross-section of the clamp system 2500 taken along the dashed line extending between G and G' (as shown on FIG. 25B). FIG. 26B illustrates the locking mechanism 727 in a locked position. As shown, the inner surface 2604 includes tapered portions 2606 that are similar to the tapered regions 745a (shown on FIG. 12 for example). As the locking mechanism 727 moves toward a distal end 2607 of the passage 2502, the tapered portions 2606 cause the portions 726a and 726b to move inward to squeeze and secure a pedicle screw, for example. A head of the pedicle screw may be inserted into a distal portion 2607 of the passage 2502 and may be retained by the clamp 726. The locking mechanism 727 may be moved into a locked position by the threaded locking cap 756 shown on FIG. 15B for example.

Figure 27B:
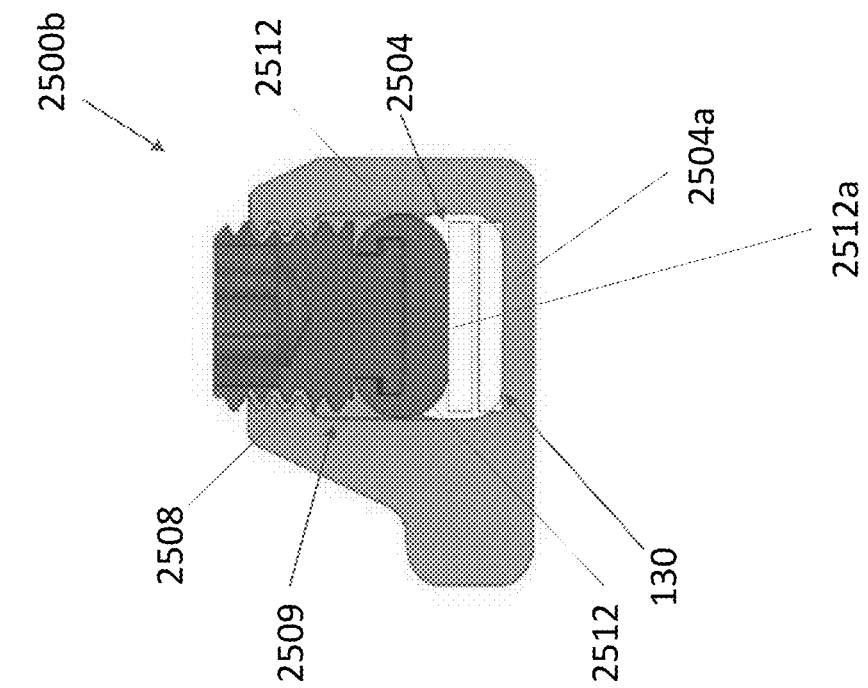
FIG. 27B is a cross-section of a second portion of the clamp system, as shown on FIG. 25B, in a locked position, in accordance with embodiments of the present disclosure.
Figure 27A:
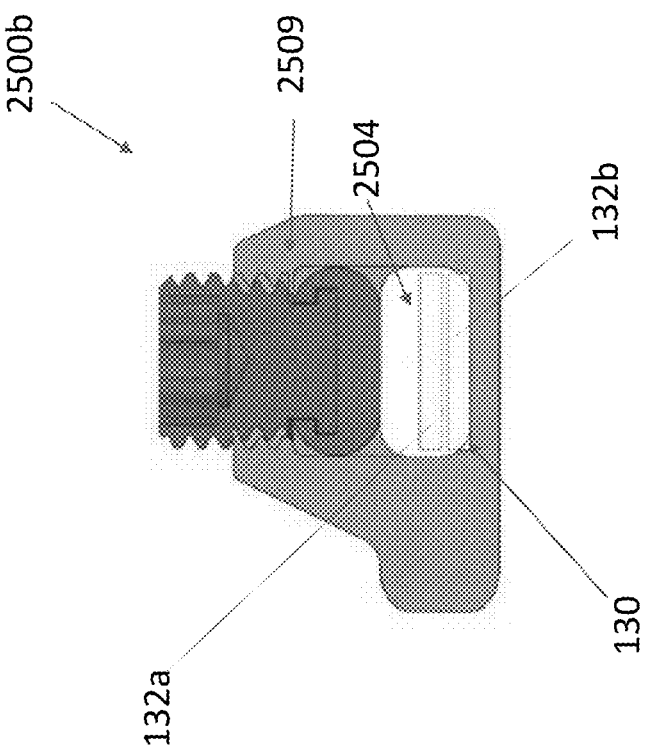
FIG. 27A is a cross-section of a second portion of the clamp system, as shown on FIG. 25B, in an unlocked position, in accordance with embodiments of the present disclosure.

FIG. 27A is a cross-section of the second portion 2500b taken along the dashed line extending between G and G' (as shown on FIG. 25B). FIG. 27A illustrates the carriage assembly 2509 in an unlocked position. As shown on FIG. 27A, the sublaminar band 130 extends through the aperture 2504. The portions 132a and 132b may be in a stacked configuration. In the unlocked position, the carriage assembly 2509 does not contact the sublaminar band 130, as shown.

FIG. 27B is a cross-section of the second portion 2500b taken along the dashed line extending between G and G' (as shown on FIG. 25B). FIG. 27A illustrates the carriage assembly 2509 in an unlocked position. As shown, the carriage assembly 2509 may be tightened thereby closing the aperture 2504. Specifically, the screw 2508 may be moved toward the sublaminar band 130 thereby causing the carriage 2512 to squeeze and secure the sublaminar band 130 within the aperture 2504, as shown on FIG. 28. That is, the sublaminar band 130 may be secured between an inner surface 2504a of the aperture 2504 and a distal end 2512a of the carriage 2512, for example.

Figure 28:
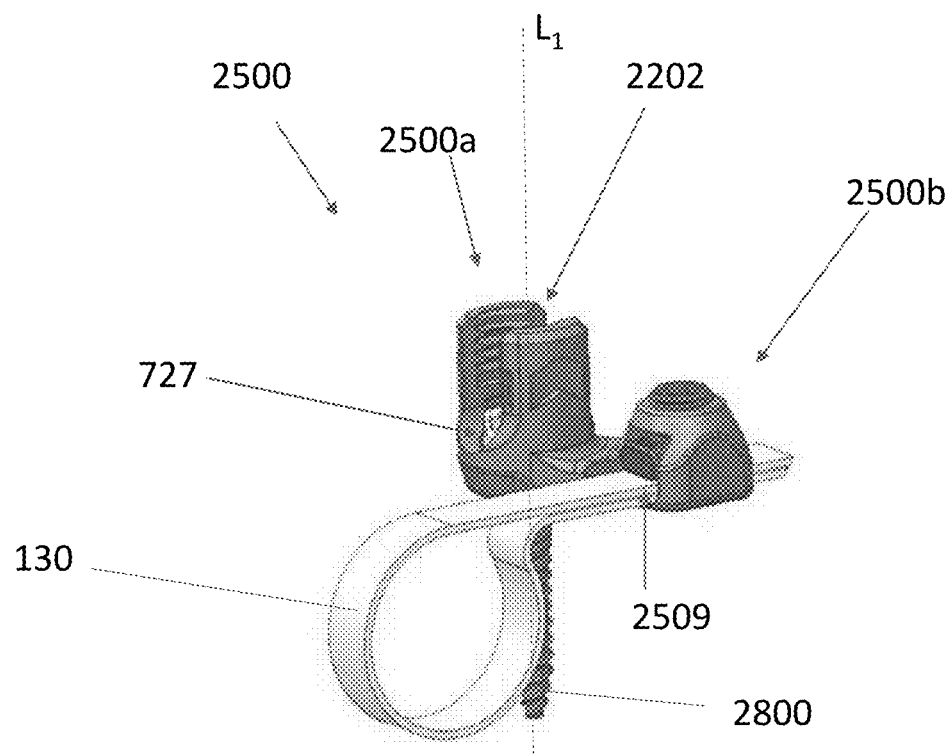
FIG. 28 illustrates a perspective view of the clamp system of FIG. 25A with a pedicle screw and a sublaminar band, in accordance with embodiments of the present disclosure.

FIG. 28 illustrates a perspective view of the clamp system 2500 with a pedicle screw 2800 and the sublaminar band 130 in accordance with particular embodiments of the present disclosure. As shown, the first and second portions 2500a and 2500b are in locked positions, thereby securing the pedicle screw 2800 to the locking mechanism 727 and securing the sublaminar band 130 to the carriage assembly 2509, as described herein. The spinal rod 128 (shown on FIG. 23 for example) may be positioned to extend through the opening 2202 such that the spinal rod 128 is perpendicular to $L_1$. Then, the threaded locking cap 756 (shown on FIG. 13B) may be disposed and tightened within the opening 2202 to secure the spinal rod 128 therein.

Figure 29:
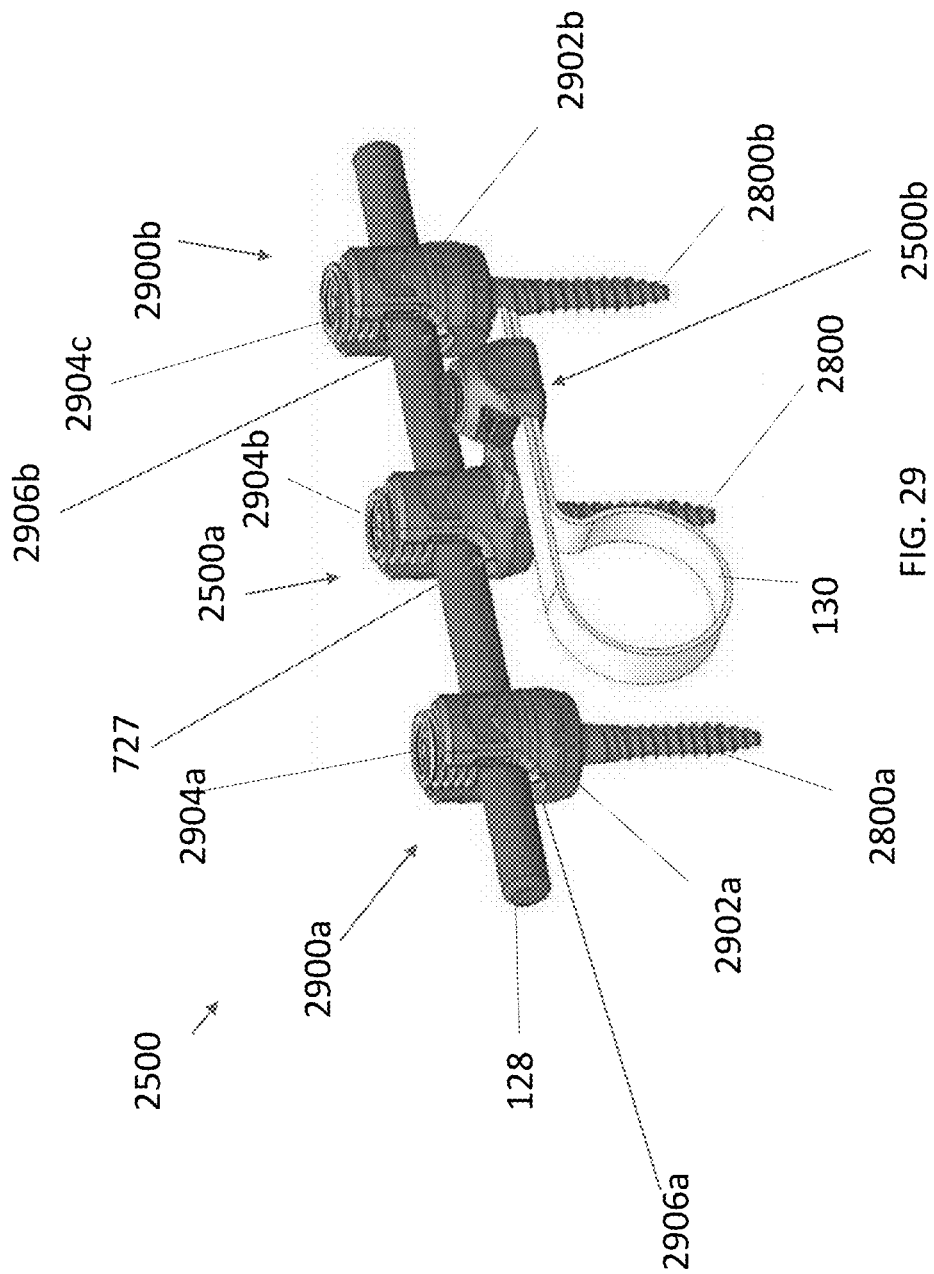
FIG. 29 illustrates the clamp system of FIG. 25A further including pedicle screw assemblies and a spinal rod, in accordance with embodiments of the present disclosure.

FIG. 29 illustrates the clamp system 2500 further including pedicle screw assemblies 2900a and 2900b and the spinal rod 128 in accordance with particular embodiments of the present disclosure. The pedicle screw assemblies 2900a and 2900b may include tulips 2902a and 2902b, as shown, that may be similar to the first portion 2500a. Threaded locking caps 2904a, 2904b, and 2904c may be disposed within pedicle the screw assemblies 2900a and 2900b and the first portion 2500a, as shown. The threaded locking caps 2904a, 2904b, and 2904c may be similar to the threaded locking cap 756, shown FIG. 13B for example.

As shown, locking mechanisms 727, 2906a and 2906b may be fastened (in a locked position) to the pedicle screws 2800, 2800a, and 2800b. The spinal rod 128 may be positioned to extend through the pedicle screw assemblies 2900a and 2900b, and through the first portion 2500a, as illustrated. The threaded locking caps 2904a, 2904b, and 2904c may be disposed and tightened to move toward the spinal rod 128 thereby securing the spinal rod 128 to the clamp system 2500. The sublaminar band 130 may extend through the second portion 2500b and may be secured therein, as previously described. The configuration of the clamp system 2500 should reduce operating time for a spinal procedure by allowing simultaneous fixations or installations of the sublaminar band 130 and the pedicle screws 2800, 2800a, and 2800b, as described herein.

Figure 30:
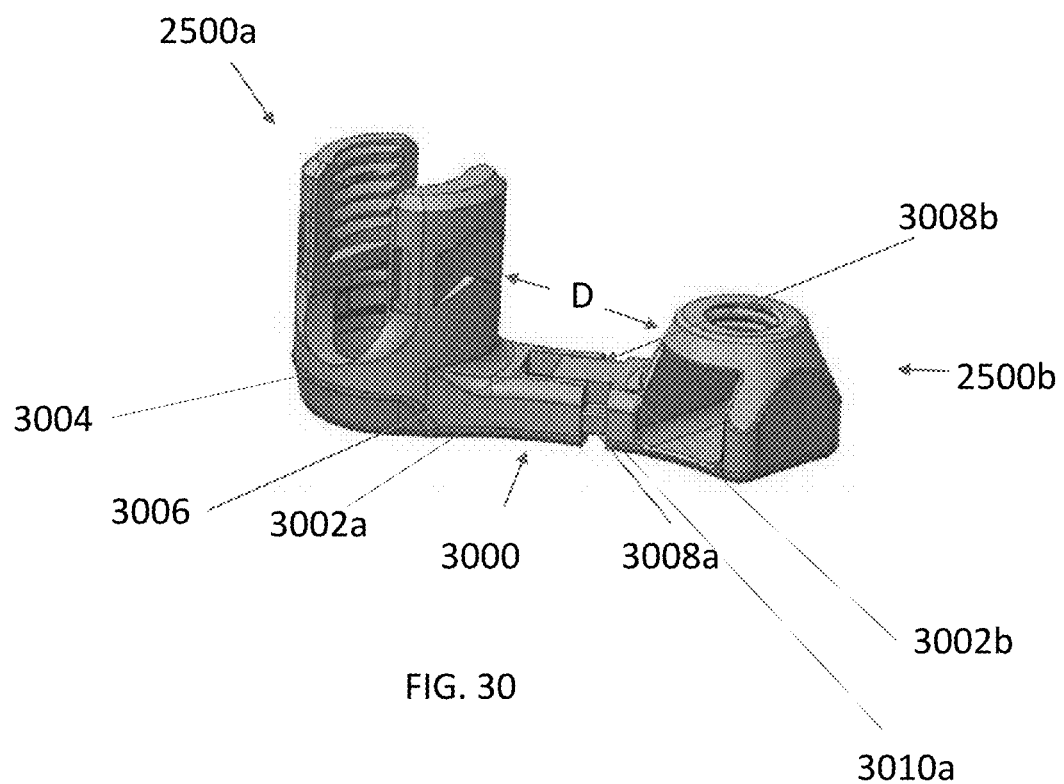
FIG. 30 illustrates a clamp system including a bridge, in accordance with embodiments of the present disclosure.

FIG. 30 illustrates the first portion 2500a coupled to the second portion 2500b by a bridge 3000, in accordance with particular embodiments of the present disclosure. The bridge 3000 may be collapsible. That is, the bridge 3000 can be adjusted to shorten a distance D between the first portion 2500a and the second portion 2500b by moving the first portion 2500a and/or the second portion 2500b toward each other. The bridge 3000 may also be extendable. That is, the bridge 3000 may be adjusted to lengthen the distance D by moving the first portion 2500a and/or the second portion 2500b away from each other. The adjustability of D should allow the clamp system 2500 to adjust to specific patient anatomy.

The bridge 3000 may include a first portion 3002a extending from an outer surface 3004 of the first portion 2500a. The first portion 3002a may include a recess 3006 comprising at least one slot 3008a. In certain embodiments, another slot may be positioned on an opposite side (opposite from the first slot 3008a) of the recess 3006. The position of the second slot is indicated by reference 3008b, as shown. The bridge 3000 may also include a second portion 3002b that may be an elongated member including at least one rail 3010a that is aligned with and extends into the slot 3008a, as shown. The second portion 3002b may also include a second rail (not shown) opposite to the first rail that extends into the second slot that indicated by the reference 3008b. In certain embodiments, the first portion 2500a may be initially separate from the second portion 2500b and may be assembled to form the clamp system 2500. That is, the clamp system 2500 may be assembled by at least inserting the rail 3010a into the slot 3008.

FIG. 31A illustrates the clamp system 2500 further including a hook 3100, in accordance with particular embodiments of the present disclosure. The hook 3100 may extend from a portion 3102 of the clamp system 2500 that may be positioned between and/or adjacent to the first portion 2500a and the second portion 2500b, as shown. The hook 3100 may include a flat surface that may taper in a direction away from the portion 3102.

FIG. 31B illustrates the clamp system 2500 with the sublaminar band 130 secured therein, in accordance with particular embodiments of the present disclosure. As shown, the sublaminar band 130 may extend through the second portion 2500b. The sublaminar band 130 may be positioned adjacent to the hook 3100. The hook 3100 may be engaged with a lamina, pedicle or transverse process of a patient before the spinal rod 128 is inserted through the first portion 2500a and secured therein.

Figure 32:
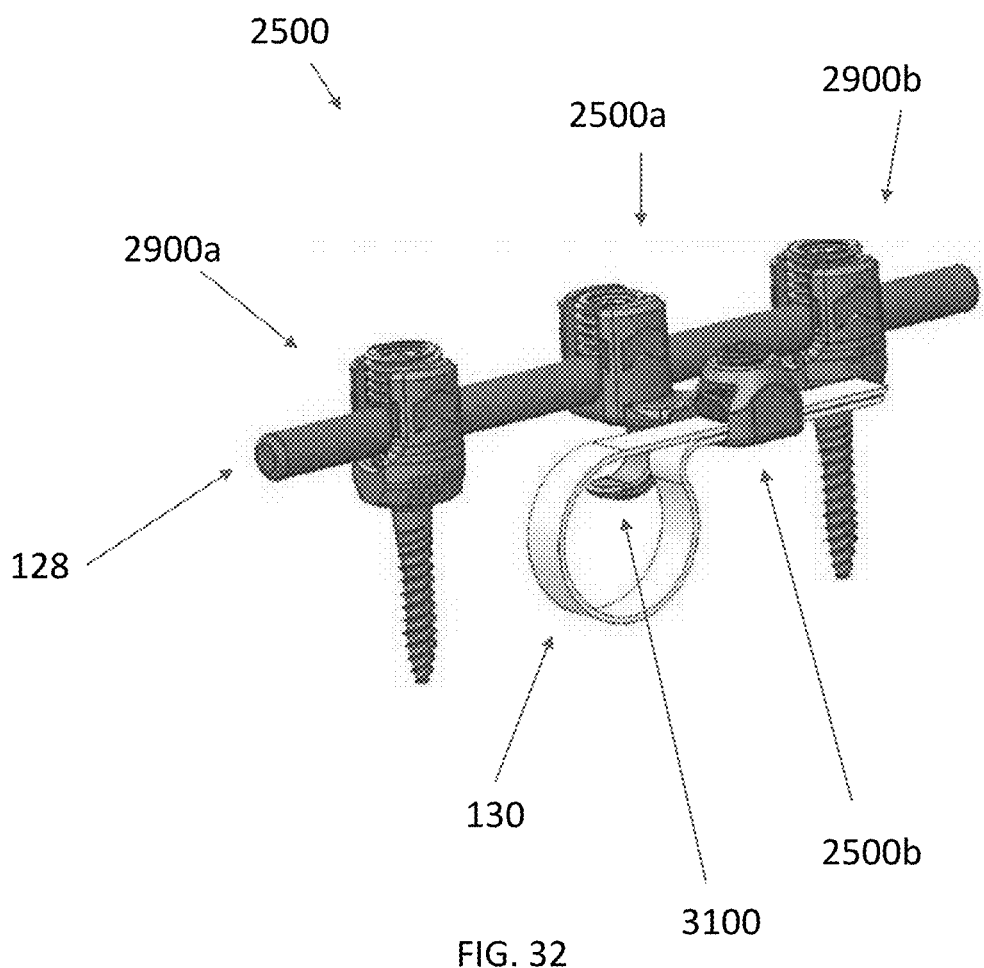
FIG. 32 illustrates the clamp system of FIG. 31A attached to a spinal rod with pedicle screw assemblies, in accordance with embodiments of the present disclosure.

FIG. 32 illustrates the clamp system 2500 and the hook 3100 attached to the spinal rod 128 along with the pedicle screw assemblies 2900a and 2900b, in accordance with particular embodiments of the present disclosure. The configuration shown in FIG. 32 may be similar to the configuration shown in FIG. 29.

As shown in a locked position, the first portion 2500a and the second portion 2500b may be disposed between the pedicle screw assemblies 2900a and 2900b. As shown, the spinal rod 128 may be retained in the clamp system 2500 via the threaded locking caps 2904a, 2904b, and 2904c. The sublaminar band 130 may be secured to the second portion 2500b. The configuration shown in FIG. 32 may allow a surgeon to create a claw construct by placing the hook 3100 on a lamina of one vertebral level and placing the sublaminar band 130 around a lamina of an adjacent vertebral level. When the sublaminar band 130 is tensioned, the two vertebral levels may be compressed together to offer an increased fixation to the claw construct.

Figure 33:
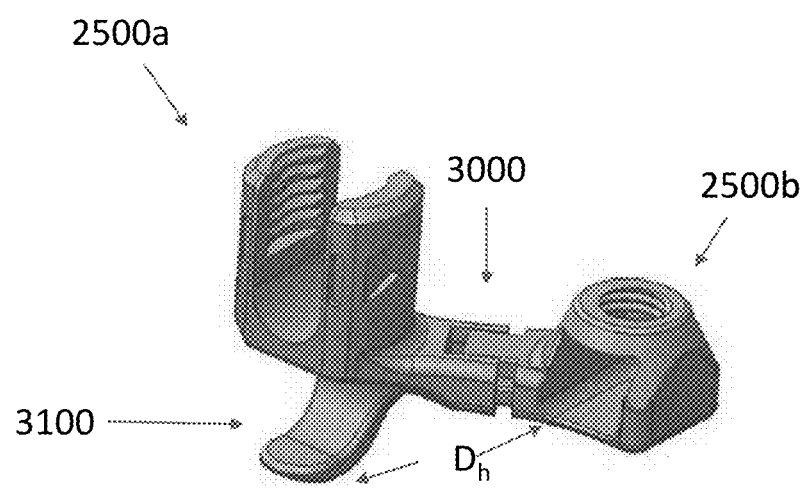
FIG. 33 illustrates a first portion of the clamp system of FIG. 30 further including a hook, in accordance with embodiments of the present disclosure.

FIG. 33 illustrates the first portion 2500a (as shown on FIG. 30) further including the hook 3100 (as shown on FIG. 31A, for example). This configuration allows a distance IA between the hook 3100 and the second portion 2500b to be adjusted due to the adjustability of the first portion 2500a relative to the second portion 2500b via the bridge 3000, as described herein. As noted previously, the first portion 2500a (including the hook 3100) may be initially separate from the second portion 2500b and may subsequently be connected to each other to form the clamp system 2500 or a portion thereof.

Figure 34:
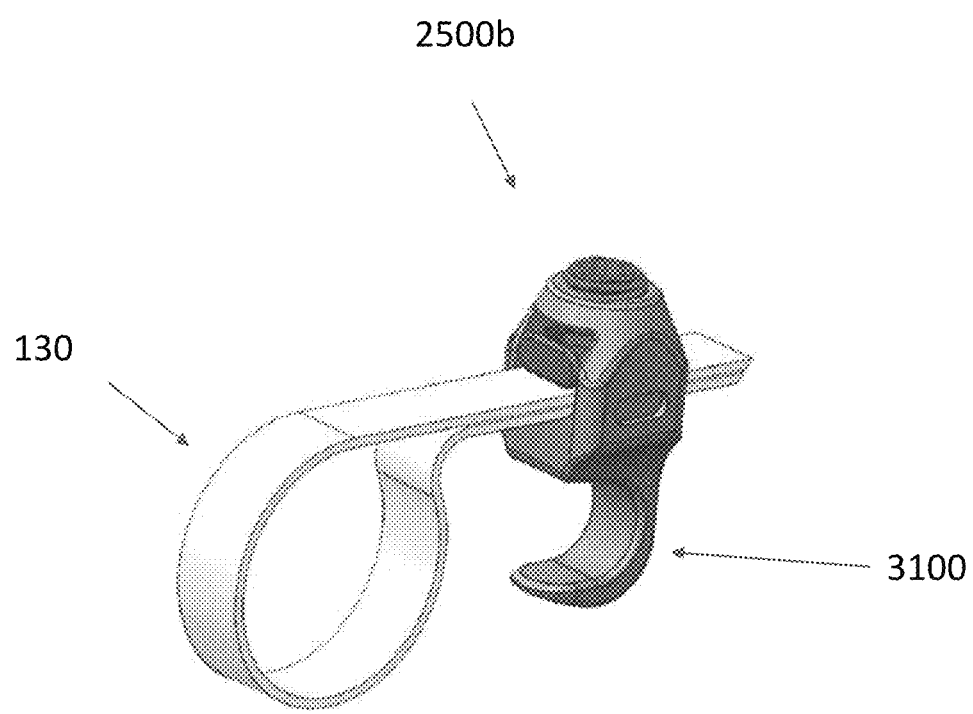
FIG. 34 illustrates a second portion of the clamp system of FIG. 30 further including a hook and a sublaminar band, in accordance with embodiments of the present disclosure.

FIG. 34 illustrates an embodiment in which the sublaminar band 130 is secured to the second portion 2500b that includes the hook 3100, in accordance with particular embodiments of the present disclosure. As shown, the hook 3100 may extend from the second portion 2500b, and the sublaminar band 130 may extend through the second portion 2500b such that the sublaminar band 130 is adjacent to the hook 3100.

The described embodiments allow surgeons to fixate the spine by securing a sublaminar band to a spinal rod construct or by securing two vertebral levels to each other. Sublaminar bands are useful when traditional pedicle screw fixation is compromised or not possible, for example in the case of patients with dysmorphic vertebrae, osteoporosis, or fractured pedicles. The embodiments described above provide a means to fixate the spine using a sublaminar band in these clinical scenarios.

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:

1. A sublaminar band clamp system comprising:
    a first locking mechanism having a first central longitudinal axis;
    a second locking mechanism having a second central longitudinal axis; and
    a body comprising:
        a first portion comprising a first passage, wherein the first locking mechanism is disposed within the first passage;
        a second portion comprising a second passage, wherein the second locking mechanism is disposed within the second passage;
        a third passage extending across the body, the third passage in fluid communication with the second passage, the third passage configured to receive a sublaminar band; and
        an opening positioned between the first and second portions, the opening in fluid communication with the first passage, the opening configured to receive a spinal rod and being only partially surrounded by the body to allow lateral loading of the spinal rod relative to a longitudinal axis of the opening,
        wherein a longitudinal axis of the first passage is generally parallel to a longitudinal axis of the third passage, and
        wherein the first central longitudinal axis of the first locking mechanism and the second central longitudinal axis of the second locking mechanism intersect the spinal rod when the spinal rod is received in the opening.

2. The sublaminar band clamp system of claim 1, wherein the first and second locking mechanisms are screws.

3. The sublaminar band clamp system of claim 1, wherein pins extend through the first passage and contact the first locking mechanism.

4. The sublaminar band clamp system of claim 1, wherein the first locking mechanism is in contact with the spinal rod.

5. The sublaminar band clamp system of claim 4, wherein the spinal rod is in contact with an inner surface of the opening.

6. The sublaminar band clamp system of claim 1, wherein an inner surface of the opening comprises teeth or grooves.

7. The sublaminar band clamp system of claim 1, further comprising the sublaminar band.

8. The sublaminar band clamp system of claim 7, wherein the second locking mechanism contacts the sublaminar band.

9. The sublaminar band clamp system of claim 8, wherein the sublaminar band contacts an inner surface of the third passage.

10. The sublaminar band clamp system of claim 1, further comprising at least one pin disposed in the body near the first locking mechanism to prevent the first locking mechanism from backing out of the first passage.

11. The sublaminar band clamp system of claim 1, further comprising a pair of pins disposed orthogonally relative to a longitudinal axis of the first passage so as to prevent the first locking mechanism from backing out of the first passage.

12. The sublaminar band clamp system of claim 1, wherein a distal end of the first locking mechanism includes a tapered portion and wherein the tapered portion of the first locking mechanism contacts the spinal rod to bias the spinal rod in the opening toward the second portion.

13. The sublaminar band clamp system of claim 1, wherein a distal end of the first locking mechanism includes a tapered portion having a protrusion and wherein the tapered portion and protrusion of the first locking mechanism contacts the spinal rod to bias the spinal rod in the opening toward the second portion.

* * * * *